United States Patent
Ganong, III et al.

(10) Patent No.: US 12,367,860 B2
(45) Date of Patent: Jul. 22, 2025

(54) SYSTEM AND METHOD FOR SECURE TRANSCRIPTION GENERATION

(71) Applicant: Microsoft Technology Licensing, LLC, Redmond, WA (US)

(72) Inventors: William F. Ganong, III, Brookline, MA (US); Uwe Helmut Jost, Groton, MA (US); Dushyant Sharma, Mountain House, CA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 435 days.

(21) Appl. No.: 17/832,323

(22) Filed: Jun. 3, 2022

(65) Prior Publication Data
US 2023/0395063 A1    Dec. 7, 2023

(51) Int. Cl.
*G10L 15/01* (2013.01)
*G10L 15/08* (2006.01)
(Continued)

(52) U.S. Cl.
CPC .............. *G10L 15/01* (2013.01); *G10L 15/08* (2013.01); *G10L 15/22* (2013.01); *G10L 21/10* (2013.01)

(58) Field of Classification Search
CPC ......... G10L 15/10; G10L 15/26; G10L 15/22; G10L 15/063; G10L 15/08; G10L 15/30; G10L 15/01; G10L 15/1815; G10L 15/20; G10L 15/02; G10L 15/04; G10L 15/187; G10L 15/183; G10L 15/19; G10L 2015/0631; G10L 2015/0635; G10L 2015/0638; G10L 2015/223; G10L 25/60; G10L 15/06; G10L 15/28; G10L 2015/0636; G10L 17/00; G10L 21/0272; G10L 13/02; G10L 2021/02166;
(Continued)

(56) References Cited

U.S. PATENT DOCUMENTS 7,584,103 B2    9/2009 Fritsch et al.
10,157,609 B2 * 12/2018 Plumpe .................. G10L 15/14
(Continued)

FOREIGN PATENT DOCUMENTS

| EP | 1939785 A2 | 7/2008 |
|----|-----------|--------|
| WO | 2006091551 A2 | 8/2006 |
| WO | WO 2006/091551 * | 8/2006 |

OTHER PUBLICATIONS

Wang et al. "Google AI Blog: Tacotron" Towards End-To-End Speech Synthesis, Apr. 6, 2017, pp. 1-10.
(Continued)

*Primary Examiner* — Abdelali Serrou
(74) *Attorney, Agent, or Firm* — Foley IP Law, PLLC

(57) ABSTRACT

A method, computer program product, and computing system for receiving an input speech signal. A transcription of the input speech signal may be generated via an automated speech recognition (ASR) system. One or more splitting points between one or more sensitive content portions and one or more non-sensitive content portions from the transcription may be identified. The input speech signal maybe split into the one or more sensitive content portions and the one or more non-sensitive content portions based upon, at least in part, the one or more splitting points, thus defining one or more sensitive content signals and one or more non-sensitive content signals.

15 Claims, 11 Drawing Sheets

(51) Int. Cl.
*G10L 15/22* (2006.01)
*G10L 21/10* (2013.01)

(58) Field of Classification Search
CPC ..... G10L 21/0208; G10L 25/45; G10L 25/51; G10L 2021/02082; G10L 13/033; G10L 13/08; G10L 15/32; G10L 17/02; G10L 17/06; G10L 2015/088; G10L 21/007; G10L 25/78; G10L 25/84; G10L 13/00; G10L 13/04; G10L 15/16; G10L 15/18; G10L 15/1822; G10L 21/00; G10L 21/01; G10L 21/0216; G10L 21/0232; G10L 21/028; G10L 21/10; G10L 25/48; G10L 17/04; G10L 19/008; G10L 19/167; G10L 2019/0001; G10L 2019/0002; G10L 2021/02087; G10L 21/02; G10L 25/12; G10L 25/24; G06F 40/30; G06F 21/6254; G06F 40/20; G06F 3/0484; G06F 21/6245; G06F 2221/2111; G06F 3/165; G06F 40/117; G06F 40/151; G06F 40/166; G06F 40/174; G06F 40/279; G06F 40/40; G06F 16/256; G06F 16/637; G06F 16/65; G06F 16/685; G06F 16/686; G06F 16/904; G06F 18/25; G06F 21/84; G06F 3/16; G06F 40/131; G06F 40/169; G06F 40/295; G06F 21/6218; G06F 40/10; G06F 40/106; G06F 40/197; G06F 40/205; G06F 40/226; G06F 40/247
See application file for complete search history.

(56) References Cited

U.S. PATENT DOCUMENTS

| | | | | |
|---|---|---|---|---|
| 2006/0041428 | A1* | 2/2006 | Fritsch | G10L 15/1815 704/E15.024 |
| 2010/0268536 | A1* | 10/2010 | Suendermann | G10L 15/22 704/E15.008 |
| 2014/0143533 | A1* | 5/2014 | Ganong, III | H04L 63/0861 713/150 |
| 2014/0207442 | A1* | 7/2014 | Ganong, III | H04W 12/02 704/201 |
| 2017/0124258 | A1* | 5/2017 | Fritsch | G16H 10/60 |
| 2019/0005952 | A1* | 1/2019 | Kruse | G10L 15/22 |
| 2019/0051375 | A1* | 2/2019 | Owen | G10L 25/48 |

OTHER PUBLICATIONS

Stubbs et al., "Automated systems for the de-identification of longitudinal clinical narratives: Overview of 2014 i2b2/UTHeath shared task Track 1," Journal of Biomedical Informatics 58 (2015), S11-S19.
Biadsy et al., "Google AI Blog: Parrotron: An End-to-End Speech Conversion Model and its Applications to Hearing-Impaired Speech and Speech Separation," Oct. 29, 2019, pp. 1-5.
U.S. Appl. No. 13/359,509, filed Jan. 27, 2012.
U.S. Appl. No. 14/850,440, filed Sep. 10, 2015.
"International Search Report and Written Opinion Issued in PCT Application No. PCT/US23/019025", Mailed Date: Aug. 3, 2023, 10 Pages.

* cited by examiner

504

| | |
|---|---|
| Doctor Jones: | Hi James, I am Doctor Jones |
| Patient James: | Hi Doctor Jones |
| Doctor Jones: | Can you please confirm your full name and date of birth? |
| Patient James: | Sure. My full name is James Alan Alexander. I was born on October 12, 1987. |
| Doctor Jones: | Great. Thank you, James. |
| Doctor Jones: | How are your migraines? Have you been regularly taking the Migraineazone four times a day that I prescribed last month? |
| Patient James: | They are much better. For a long time it was difficult to work but the Migraineazone is helping. I did have a question about side effects. |

| | |
|---|---|
| Doctor James: | Hi Jason, I am Doctor James |
| Patient Jason: | Hi Doctor James |
| Doctor James: | Can you please confirm your full name and date of birth? |
| Patient Jason: | Sure. My full name is Jason Aaron Alexander. I was born on November 12, 1997. |
| Doctor James: | Great. Thank you, Jason. |
| Doctor James: | How are your migraines? Have you been regularly taking the Migraineazone two times a day that I prescribed last month? |
| Patient Jason: | They are much better. For a long time it was difficult to work but the Migraineazone is helping. I did have a question about side effects. |

FIG. 7

SYSTEM AND METHOD FOR SECURE TRANSCRIPTION GENERATION

BACKGROUND

Automated Clinical Documentation (ACD) may be used, e.g., to turn transcribed conversational (e.g., physician, patient, and/or other participants such as patient's family members, nurses, physician assistants, etc.) speech into formatted (e.g., medical) reports. Such reports may be reviewed, e.g., to assure accuracy of the reports by the physician, scribe, etc.

However, when transcribing audio data containing sensitive information, there is a risk for data breaches. This may be particularly true if the audio data is transcribed outside of a firewall, e.g. by contractors or quality documentation specialists (QDSs). Accordingly, the ability to generate accurate transcriptions may be vulnerable to breaches of confidential and sensitive information.

BRIEF DESCRIPTION OF THE DRAWINGS

FIGS. 6-7 are example transcriptions according to various implementations of the transcription generation process of FIG. 1;

Like reference symbols in the various drawings indicate like elements.

DETAILED DESCRIPTION OF THE PREFERRED EMBODIMENTS

As discussed above, when transcribing audio data containing sensitive information, there is a risk for data breaches. This may be particularly true if the audio data is transcribed outside of a firewall and/or is provided to others, e.g. by contractors or quality documentation specialists (QDSs). Accordingly, the ability to generate accurate transcriptions may be vulnerable to breaches of confidential and sensitive information. For example, snippets of speech long enough to identify a speaker may be considered personally identifiable information (PII) (e.g., as defined by the General Data Protection Regulation (GDPR)), because the speaker can be identified. Additionally, snippets of speech and the corresponding text of a transcription may include other sensitive information (e.g., patient names, phone numbers, credit card numbers, etc.).

Accordingly, there are at least two breach scenarios during transcription generation that may be addressed by the present disclosure: a disclosure of sensitive content by a labeler or by an internal actor. A labeler is an external entity or system that is tasked with labeling or transcribing audio data. A labeler typically sees only a small portion of the total audio data. However, there are generally many labelers, and securing their cooperation, and all their computers, could be quite challenging. An internal actor could potentially scan lots of internal data (e.g., by looking for particular persons or classes of information, such as credit card numbers). As will be discussed in greater detail below, implementations of the present disclosure provide a technical solution necessarily rooted in computing technology to provide secure transcription generation. Specifically, implementations of the present disclosure may automatically (via automated speech recognition (ASR), natural language understanding (NLU), and other speech processing systems) securely generate transcriptions without exposing sensitive content. In this manner, implementations of the present disclosure may allow for manual labeling of input speech data for training speech processing systems or models without breaching sensitive content within the input speech signals.

The details of one or more implementations are set forth in the accompanying drawings and the description below. Other features and advantages will become apparent from the description, the drawings, and the claims.

System Overview

Figure 1:
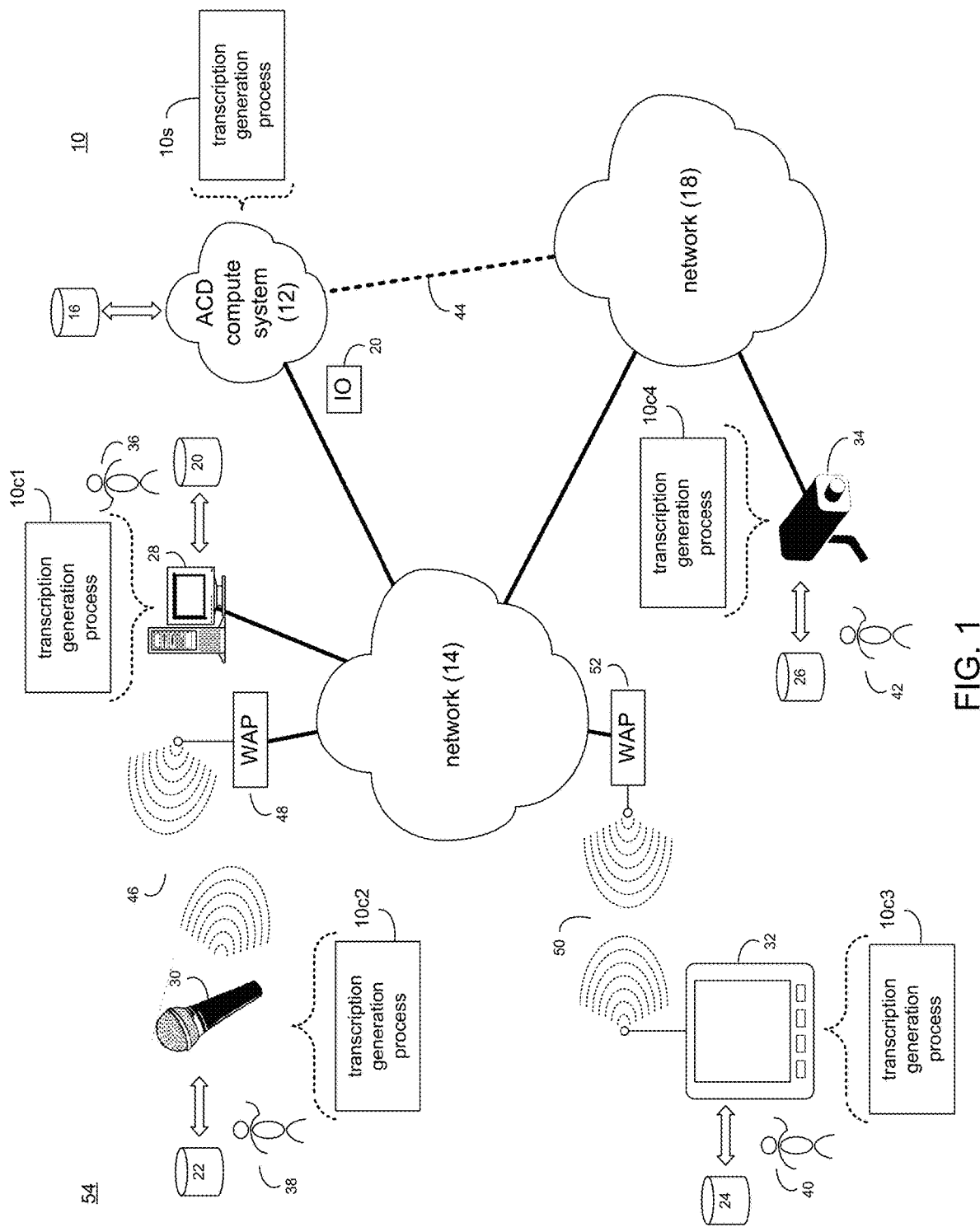
FIG. 1 is a diagrammatic view of an automated clinical documentation computer system and a transcription generation process coupled to a distributed computing network.

Referring to FIG. 1, there is shown transcription generation process 10. Transcription generation process 10 may be implemented as a server-side process, a client-side process, or a hybrid server-side/client-side process. For example, transcription generation process 10 may be implemented as a purely server-side process via transcription generation process 10s. Alternatively, transcription generation process 10 may be implemented as a purely client-side process via one or more of transcription generation process 10c1, transcription generation process 10c2, transcription generation process 10c3, and transcription generation process 10c4. Alternatively still, transcription generation process 10 may be implemented as a hybrid server-side/client-side process via transcription generation process 10s in combination with one or more of transcription generation process 10c1, transcription generation process 10c2, transcription generation process 10c3, and transcription generation process 10c4.

Accordingly, transcription generation process 10 as used in this disclosure may include any combination of transcription generation process 10s, transcription generation process 10c1, transcription generation process 10c2, transcription generation process 10c3, and transcription generation process 10c4.

Transcription generation process 10s may be a server application and may reside on and may be executed by automated clinical documentation (ACD) computer system 12, which may be connected to network 14 (e.g., the Internet or a local area network). ACD computer system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

As is known in the art, a SAN may include one or more of a personal computer, a server computer, a series of server computers, a mini computer, a mainframe computer, a RAID device and a NAS system. The various components of ACD computer system 12 may execute one or more operating systems, examples of which may include but are not limited to: Microsoft Windows Server™; Redhat Linux™, Unix, or a custom operating system, for example.

The instruction sets and subroutines of transcription generation process 10s, which may be stored on storage device 16 coupled to ACD computer system 12, may be executed by one or more processors (not shown) and one or more memory architectures (not shown) included within ACD computer system 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Various IO requests (e.g. IO request 20) may be sent from transcription generation process 10s, transcription generation process 10c1, transcription generation process 10c2, transcription generation process 10c3 and/or transcription generation process to ACD computer system 12. Examples of IO request 20 may include but are not limited to data write requests (i.e. a request that content be written to ACD computer system 12) and data read requests (i.e. a request that content be read from ACD computer system 12).

The instruction sets and subroutines of transcription generation process 10c1, transcription generation process 10c2, transcription generation process 10c3 and/or transcription generation process 10c4, which may be stored on storage devices 20, 22, 24, 26 (respectively) coupled to ACD client electronic devices 28, 30, 32, 34 (respectively), may be executed by one or more processors (not shown) and one or more memory architectures (not shown) incorporated into ACD client electronic devices 28, 30, 32, 34 (respectively). Storage devices 20, 22, 24, 26 may include but are not limited to: hard disk drives; optical drives; RAID devices; random access memories (RAM); read-only memories (ROM), and all forms of flash memory storage devices. Examples of ACD client electronic devices 28, 30, 32, 34 may include, but are not limited to, personal computing device 28 (e.g., a smart phone, a personal digital assistant, a laptop computer, a notebook computer, and a desktop computer), audio input device 30 (e.g., a handheld microphone, a lapel microphone, an embedded microphone (such as those embedded within eyeglasses, smart phones, tablet computers and/or watches) and an audio recording device), display device 32 (e.g., a tablet computer, a computer monitor, and a smart television), machine vision input device 34 (e.g., an RGB imaging system, an infrared imaging system, an ultraviolet imaging system, a laser imaging system, a SONAR imaging system, a RADAR imaging system, and a thermal imaging system), a hybrid device (e.g., a single device that includes the functionality of one or more of the above-references devices; not shown), an audio rendering device (e.g., a speaker system, a headphone system, or an earbud system; not shown), various medical devices (e.g., medical imaging equipment, heart monitoring machines, body weight scales, body temperature thermometers, and blood pressure machines; not shown), and a dedicated network device (not shown).

Users 36, 38, 40, 42 may access ACD computer system 12 directly through network 14 or through secondary network 18. Further, ACD computer system 12 may be connected to network 14 through secondary network 18, as illustrated with link line 44.

The various ACD client electronic devices (e.g., ACD client electronic devices 28, 30, 32, 34) may be directly or indirectly coupled to network 14 (or network 18). For example, personal computing device 28 is shown directly coupled to network 14 via a hardwired network connection. Further, machine vision input device 34 is shown directly coupled to network 18 via a hardwired network connection. Audio input device 30 is shown wirelessly coupled to network 14 via wireless communication channel 46 established between audio input device 30 and wireless access point (i.e., WAP) 48, which is shown directly coupled to network 14. WAP 48 may be, for example, an IEEE 802.11a, 802.11b, 802.11g, 802.11n, Wi-Fi, and/or Bluetooth device that is capable of establishing wireless communication channel 46 between audio input device 30 and WAP 48. Display device 32 is shown wirelessly coupled to network 14 via wireless communication channel established between display device 32 and WAP 52, which is shown directly coupled to network 14.

The various ACD client electronic devices (e.g., ACD client electronic devices 28, 30, 32, 34) may each execute an operating system, examples of which may include but are not limited to Microsoft Windows™, Apple Macintosh™, Redhat Linux™, or a custom operating system, wherein the combination of the various ACD client electronic devices (e.g., ACD client electronic devices 28, 30, 32, 34) and ACD computer system 12 may form modular ACD system 54.

Figure 2:
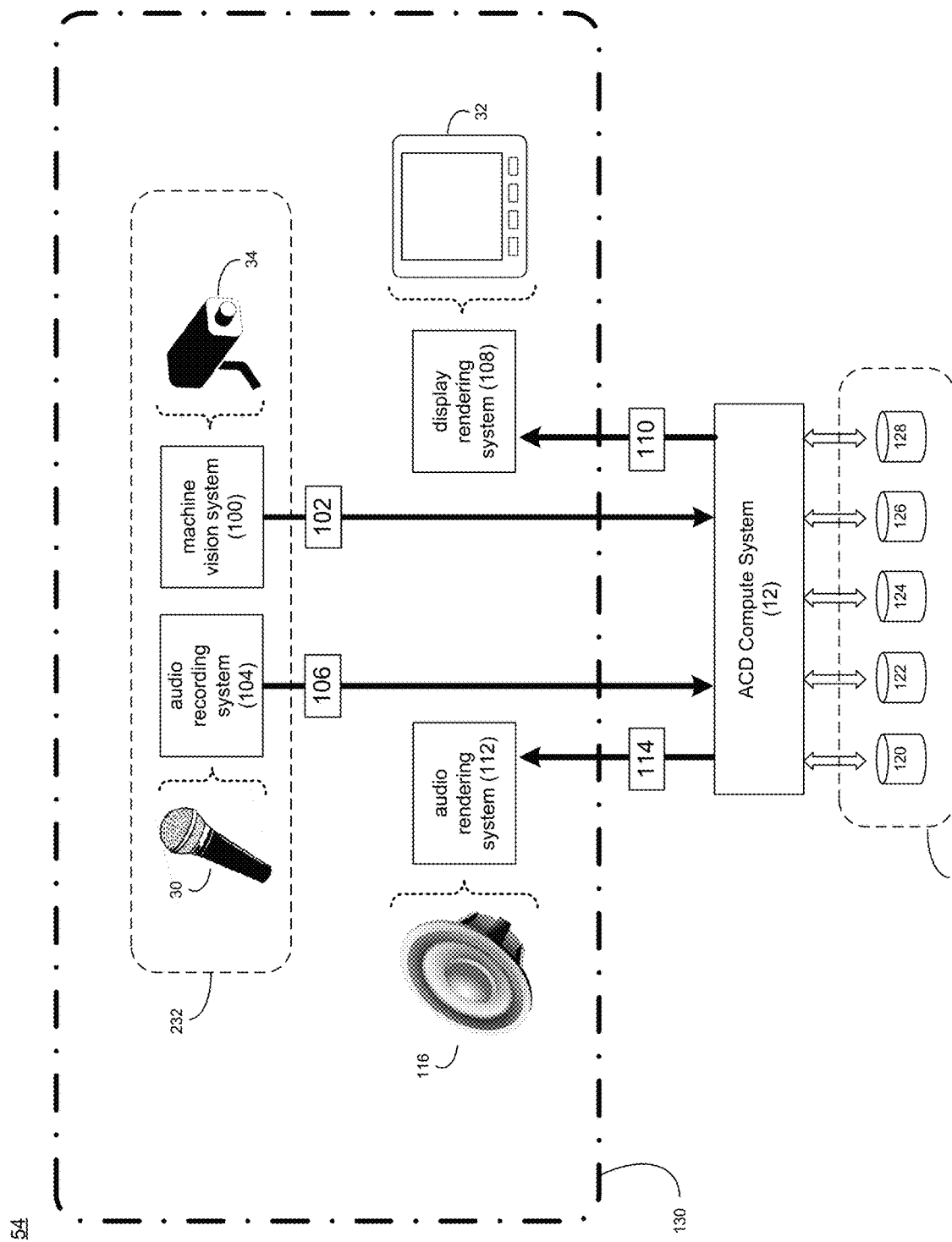
FIG. 2 is a diagrammatic view of a modular ACD system incorporating the automated clinical documentation computer system of FIG. 1.

Referring also to FIG. 2, there is shown a simplified example embodiment of modular ACD system 54 that is configured to automate clinical documentation. Modular ACD system 54 may include: machine vision system 100 configured to obtain machine vision encounter information 102 concerning a patient encounter; audio recording system 104 configured to obtain audio encounter information 106 concerning the patient encounter; and a computer system (e.g., ACD computer system 12) configured to receive machine vision encounter information 102 and audio encounter information 106 from machine vision system 100 and audio recording system 104 (respectively). Modular ACD system 54 may also include: display rendering system 108 configured to render visual information 110; and audio rendering system 112 configured to render audio information 114, wherein ACD computer system 12 may be configured to provide visual information 110 and audio information 114 to display rendering system 108 and audio rendering system 112 (respectively).

Example of machine vision system 100 may include but are not limited to: one or more ACD client electronic devices (e.g., ACD client electronic device 34, examples of which may include but are not limited to an RGB imaging system, an infrared imaging system, a ultraviolet imaging system, a laser imaging system, a SONAR imaging system, a RADAR imaging system, and a thermal imaging system). Examples of audio recording system 104 may include but are not limited to: one or more ACD client electronic devices (e.g., ACD client electronic device 30, examples of which may include but are not limited to a handheld microphone, a lapel microphone, an embedded microphone (such as those embedded within eyeglasses, smart phones, tablet computers and/or watches) and an audio recording device). Examples of display rendering system 108 may include but are not limited to: one or more ACD client electronic devices (e.g., ACD client electronic device 32, examples of which may include but are not limited to a tablet computer, a computer monitor, and a smart television). Examples of audio rendering system 112 may include but are not limited to: one or more ACD client electronic devices (e.g., audio rendering device 116, examples of which may include but are not limited to a speaker system, a headphone system, and an earbud system).

As will be discussed below in greater detail, ACD computer system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource. While in this particular example, five different examples of datasources 118, are shown, this is for illustrative purposes only and is not intended to be a limitation of this disclosure, as other configurations are possible and are considered to be within the scope of this disclosure.

As will be discussed below in greater detail, modular ACD system 54 may be configured to monitor a monitored space (e.g., monitored space 130) in a clinical environment, wherein examples of this clinical environment may include but are not limited to: a doctor's office, a medical facility, a medical practice, a medical lab, an urgent care facility, a medical clinic, an emergency room, an operating room, a hospital, a long term care facility, a rehabilitation facility, a nursing home, and a hospice facility. Accordingly, an example of the above-referenced patient encounter may include but is not limited to a patient visiting one or more of the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility).

Machine vision system 100 may include a plurality of discrete machine vision systems when the above-described clinical environment is larger or a higher level of resolution is desired. As discussed above, examples of machine vision system 100 may include but are not limited to: one or more ACD client electronic devices (e.g., ACD client electronic device 34, examples of which may include but are not limited to an RGB imaging system, an infrared imaging system, an ultraviolet imaging system, a laser imaging system, a SONAR imaging system, a RADAR imaging system, and a thermal imaging system). Accordingly, machine vision system 100 may include one or more of each of an RGB imaging system, an infrared imaging systems, an ultraviolet imaging systems, a laser imaging system, a SONAR imaging system, a RADAR imaging system, and a thermal imaging system.

Audio recording system 104 may include a plurality of discrete audio recording systems when the above-described clinical environment is larger or a higher level of resolution is desired. As discussed above, examples of audio recording system 104 may include but are not limited to: one or more ACD client electronic devices (e.g., ACD client electronic device 30, examples of which may include but are not limited to a handheld microphone, a lapel microphone, an embedded microphone (such as those embedded within eyeglasses, smart phones, tablet computers and/or watches) and an audio recording device). Accordingly, audio recording system 104 may include one or more of each of a handheld microphone, a lapel microphone, an embedded microphone (such as those embedded within eyeglasses, smart phones, tablet computers and/or watches) and an audio recording device.

Display rendering system 108 may include a plurality of discrete display rendering systems when the above-described clinical environment is larger or a higher level of resolution is desired. As discussed above, examples of display rendering system 108 may include but are not limited to: one or more ACD client electronic devices (e.g., ACD client electronic device 32, examples of which may include but are not limited to a tablet computer, a computer monitor, and a smart television). Accordingly, display rendering system 108 may include one or more of each of a tablet computer, a computer monitor, and a smart television.

Audio rendering system 112 may include a plurality of discrete audio rendering systems when the above-described clinical environment is larger or a higher level of resolution is desired. As discussed above, examples of audio rendering system 112 may include but are not limited to: one or more ACD client electronic devices (e.g., audio rendering device 116, examples of which may include but are not limited to a speaker system, a headphone system, or an earbud system). Accordingly, audio rendering system 112 may include one or more of each of a speaker system, a headphone system, or an earbud system.

ACD computer system 12 may include a plurality of discrete computer systems. As discussed above, ACD computer system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform. Accordingly, ACD computer system 12 may include one or more of each of a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

Figure 3:
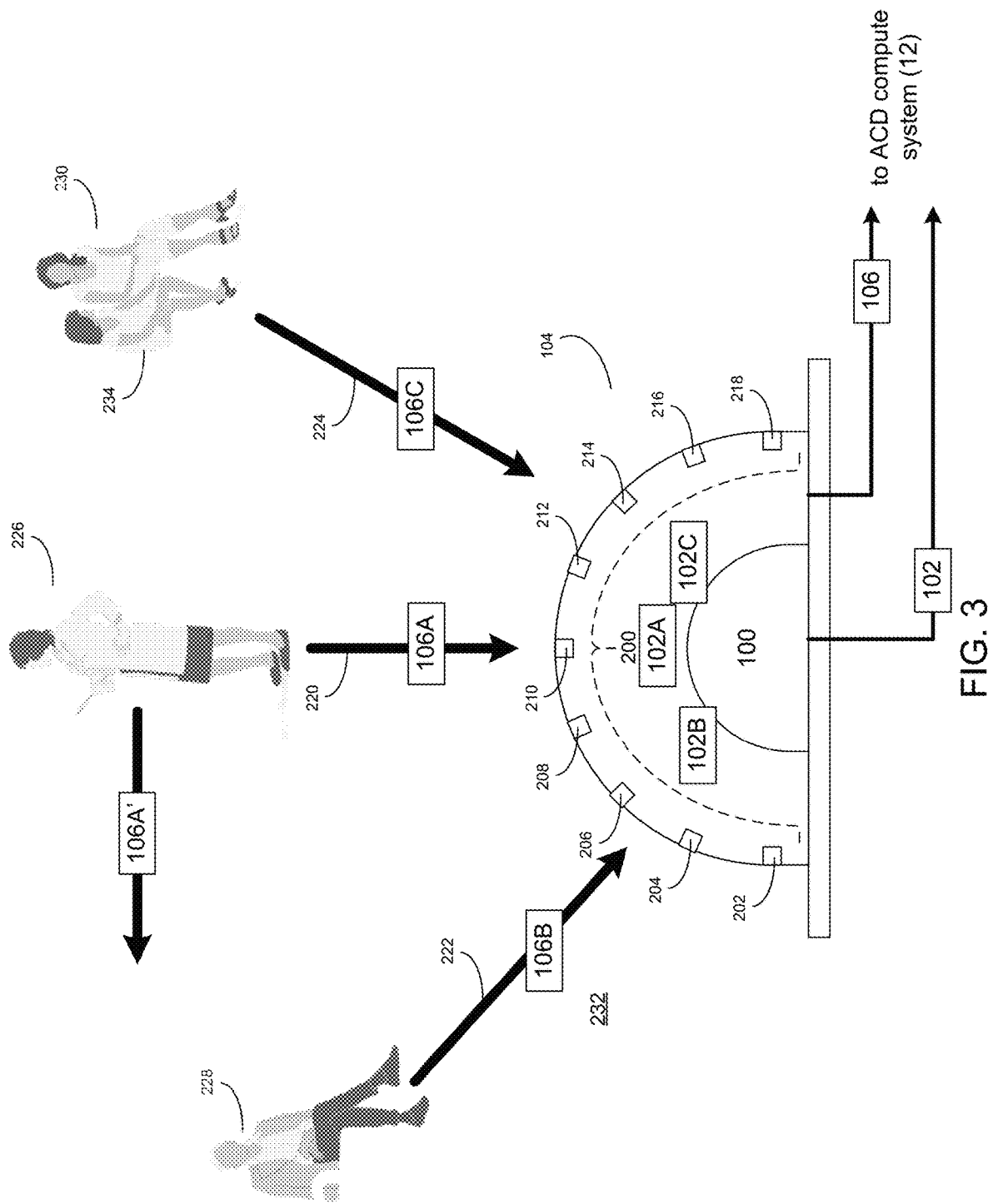
FIG. 3 is a diagrammatic view of a mixed-media ACD device included within the modular ACD system of FIG. 2.
Figure 4:
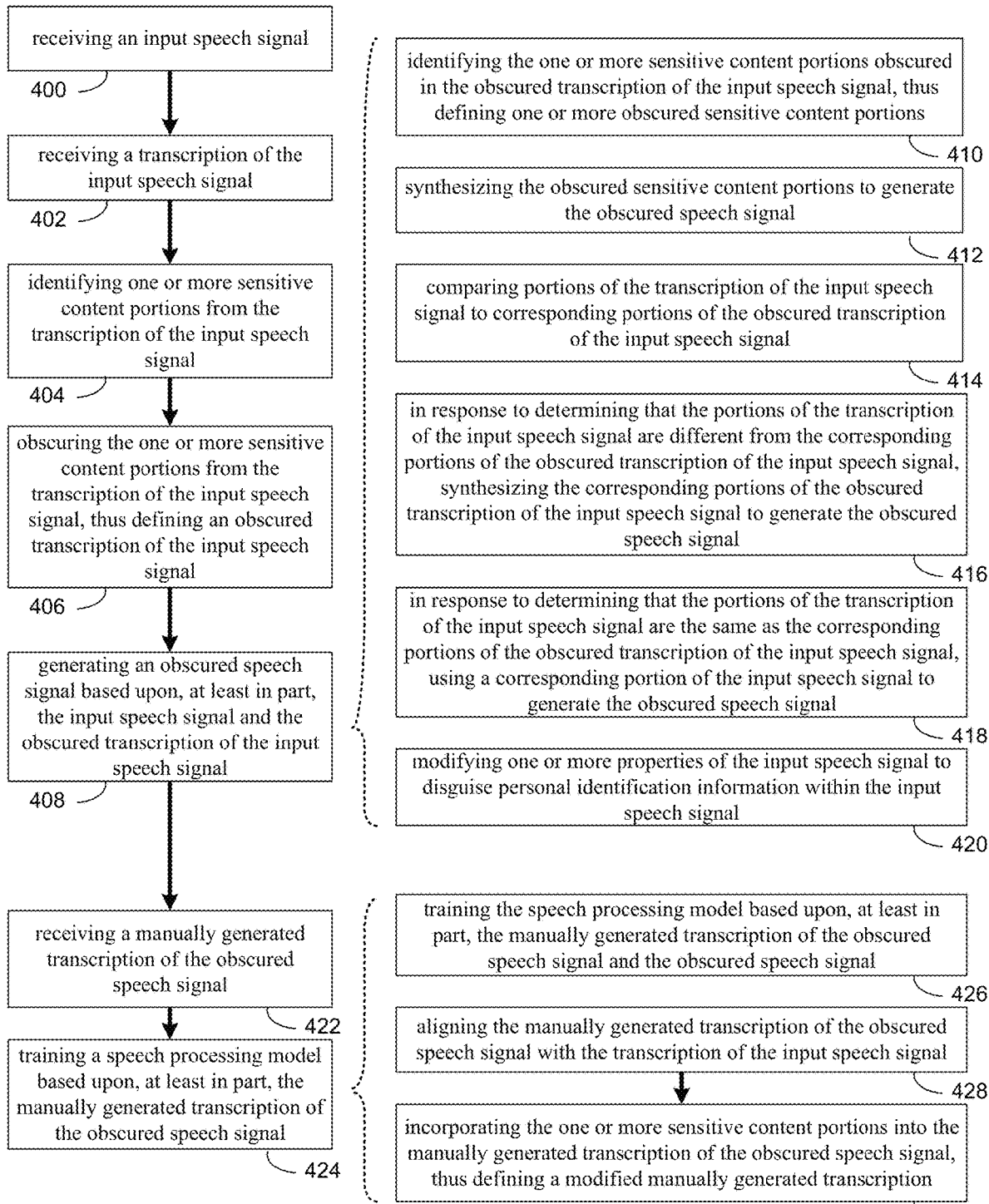
FIG. 4 is a flow chart of one implementation of the transcription generation process of FIG. 1.

Referring also to FIG. 3, audio recording system 104 may include directional microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. As will be discussed below in greater detail, modular ACD system 54 may be configured to form one or more audio recording beams (e.g., audio recording beams 220, 222, 224) via the discrete audio acquisition devices (e.g., audio acquisition devices 202, 204, 206, 208, 210, 212, 214, 216, 218) included within audio recording system 104.

For example, modular ACD system 54 may be further configured to steer the one or more audio recording beams (e.g., audio recording beams 220, 222, 224) toward one or more encounter participants (e.g., encounter participants 226, 228, 230) of the above-described patient encounter.

Examples of the encounter participants (e.g., encounter participants 226, 228, 230) may include but are not limited to: medical professionals (e.g., doctors, nurses, physician's assistants, lab technicians, physical therapists, scribes (e.g., a transcriptionist) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

Accordingly, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam. For example, modular ACD system 54 and/or audio recording system 104 may be configured to utilize audio acquisition device 210 to form audio recording beam 220, thus enabling the capturing of audio (e.g., speech) produced by encounter participant 226 (as audio acquisition device 210 is pointed to (i.e., directed toward) encounter participant 226). Additionally, modular ACD system 54 and/or audio recording system 104 may be configured to utilize audio acquisition devices 204, 206 to form audio recording beam 222, thus enabling the capturing of audio (e.g., speech) produced by encounter participant 228 (as audio acquisition devices 204, 206 are pointed to (i.e., directed toward) encounter participant 228). Additionally, modular ACD system 54 and/or audio recording system 104 may be configured to utilize audio acquisition devices 212, 214 to form audio recording beam 224, thus enabling the capturing of audio (e.g., speech) produced by encounter participant 230 (as audio acquisition devices 212, 214 are pointed to (i.e., directed toward) encounter participant 230). Further, modular ACD system 54 and/or audio recording system 104 may be configured to utilize null-steering precoding to cancel interference between speakers and/or noise.

As is known in the art, null-steering precoding is a method of spatial signal processing by which a multiple antenna transmitter may null multiuser interference signals in wireless communications, wherein null-steering precoding may mitigate the impact off background noise and unknown user interference.

In particular, null-steering precoding may be a method of beamforming for narrowband signals that may compensate for delays of receiving signals from a specific source at different elements of an antenna array. In general and to improve performance of the antenna array, in incoming signals may be summed and averaged, wherein certain signals may be weighted and compensation may be made for signal delays.

Machine vision system 100 and audio recording system 104 may be stand-alone devices (as shown in FIG. 2). Additionally/alternatively, machine vision system 100 and audio recording system 104 may be combined into one package to form mixed-media ACD device 232. For example, mixed-media ACD device 232 may be configured to be mounted to a structure (e.g., a wall, a ceiling, a beam, a column) within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility), thus allowing for easy installation of the same. Further, modular ACD system 54 may be configured to include a plurality of mixed-media ACD devices (e.g., mixed-media ACD device 232) when the above-described clinical environment is larger or a higher level of resolution is desired.

Modular ACD system 54 may be further configured to steer the one or more audio recording beams (e.g., audio recording beams 220, 222, 224) toward one or more encounter participants (e.g., encounter participants 226, 228, 230) of the patient encounter based, at least in part, upon machine vision encounter information 102. As discussed above, mixed-media ACD device 232 (and machine vision system 100/audio recording system 104 included therein) may be configured to monitor one or more encounter participants (e.g., encounter participants 226, 228, 230) of a patient encounter.

Specifically, machine vision system 100 (either as a stand-alone system or as a component of mixed-media ACD device 232) may be configured to detect humanoid shapes within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility). And when these humanoid shapes are detected by machine vision system 100, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam (e.g., audio recording beams 220, 222, 224) that is directed toward each of the detected humanoid shapes (e.g., encounter participants 226, 228, 230).

As discussed above, ACD computer system 12 may be configured to receive machine vision encounter information 102 and audio encounter information 106 from machine vision system 100 and audio recording system 104 (respectively); and may be configured to provide visual information 110 and audio information 114 to display rendering system 108 and audio rendering system 112 (respectively). Depending upon the manner in which modular ACD system 54 (and/or mixed-media ACD device 232) is configured, ACD computer system 12 may be included within mixed-media ACD device 232 or external to mixed-media ACD device 232.

As discussed above, ACD computer system 12 may execute all or a portion of transcription generation process 10, wherein the instruction sets and subroutines of transcription generation process 10 (which may be stored on one or more of e.g., storage devices 16, 20, 22, 24, 26) may be executed by ACD computer system 12 and/or one or more of ACD client electronic devices 28, 30, 32, 34.

The Transcription Generation Process

As discussed above, when transcribing audio data containing sensitive information, there is a risk for data breaches. This may be particularly true if the audio data is transcribed outside of a firewall and/or is provided to others, e.g. by contractors or quality documentation specialists (QDSs). Accordingly, the ability to generate accurate transcriptions may be vulnerable to breaches of confidential and sensitive information. For example, snippets of speech long enough to identify a speaker may be considered personally identifiable information (PII) (e.g., as defined by the General Data Protection Regulation (GDPR)), because the speaker can be identified. Additionally, snippets of speech and the corresponding text of a transcription may include other sensitive information (e.g., patient names, phone numbers, credit card numbers, etc.).

Accordingly, there are at least two breach scenarios during transcription generation that may be addressed by the present disclosure: a disclosure of sensitive content by a labeler or by an internal actor. A labeler is an external entity or system that is tasked with labeling or transcribing audio data. A labeler typically sees only a small portion of the total audio data. However, there are generally many labelers, and securing their cooperation, and all their computers, could be quite challenging. An internal actor could potentially scan lots of internal data (e.g., by looking for particular persons or classes of information, such as credit card numbers). As will be discussed in greater detail below, implementations of the present disclosure provide a technical solution necessarily rooted in computing technology to provide secure transcription generation. Specifically, implementations of the present disclosure may automatically (via automated speech recognition (ASR), natural language understanding (NLU), and other speech processing systems) securely generate transcriptions without exposing sensitive content. In this manner, implementations of the present disclosure may allow for manual labeling of input speech data for training speech processing systems or models without breaching sensitive content within the input speech signals.

Referring also at least to FIGS. 4-9, transcription generation process 10 may receive 400 an input speech signal. A transcription of the input speech signal may be received 402. One or more sensitive content portions may be identified 404 from the transcription of the input speech signal. The one or more sensitive content portions from the transcription of the input speech signal may be obscured 406, thus defining an obscured transcription of the input speech signal. An obscured speech signal may be generated 408 based upon, at least in part, the input speech signal and the obscured transcription of the input speech signal.

In some implementations consistent with the present disclosure, systems and methods may be provided for generating a new kind of speech "transcoder", with three inputs: an original speech signal, a transcription of the original speech signal, and a modified transcription, with sensitive content obscured. As will be described in greater detail below, this transcoder may generate an obscured speech signal by "transcoding" the speech to a standard speaker when the transcription is not modified; but when the transcription is modified, the transcoder may create synthetic speech, also consistent with the standard speaker.

Figure 5:
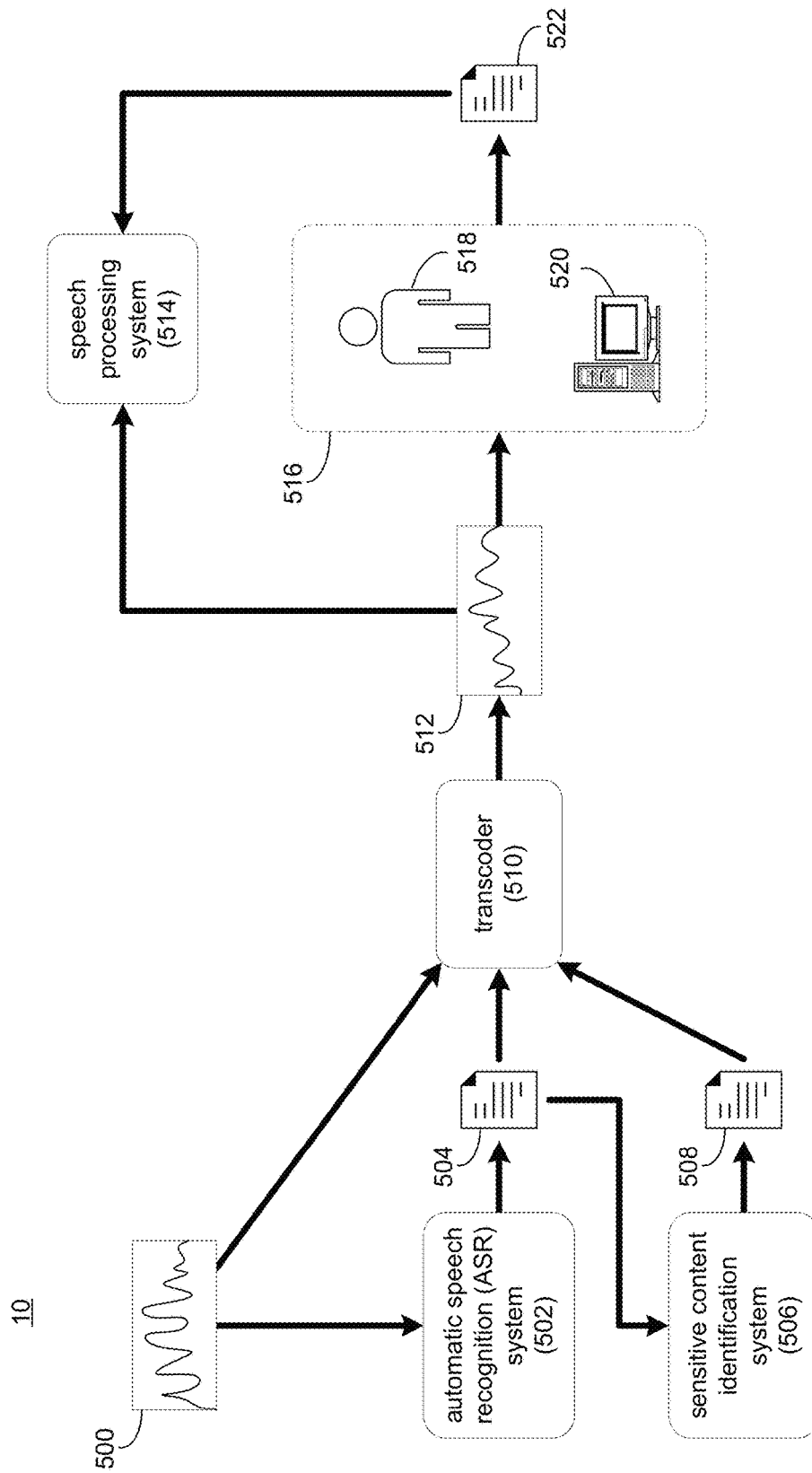
FIG. 5 is a diagrammatic view of the transcription generation process of FIG. 1.
Figure 8:
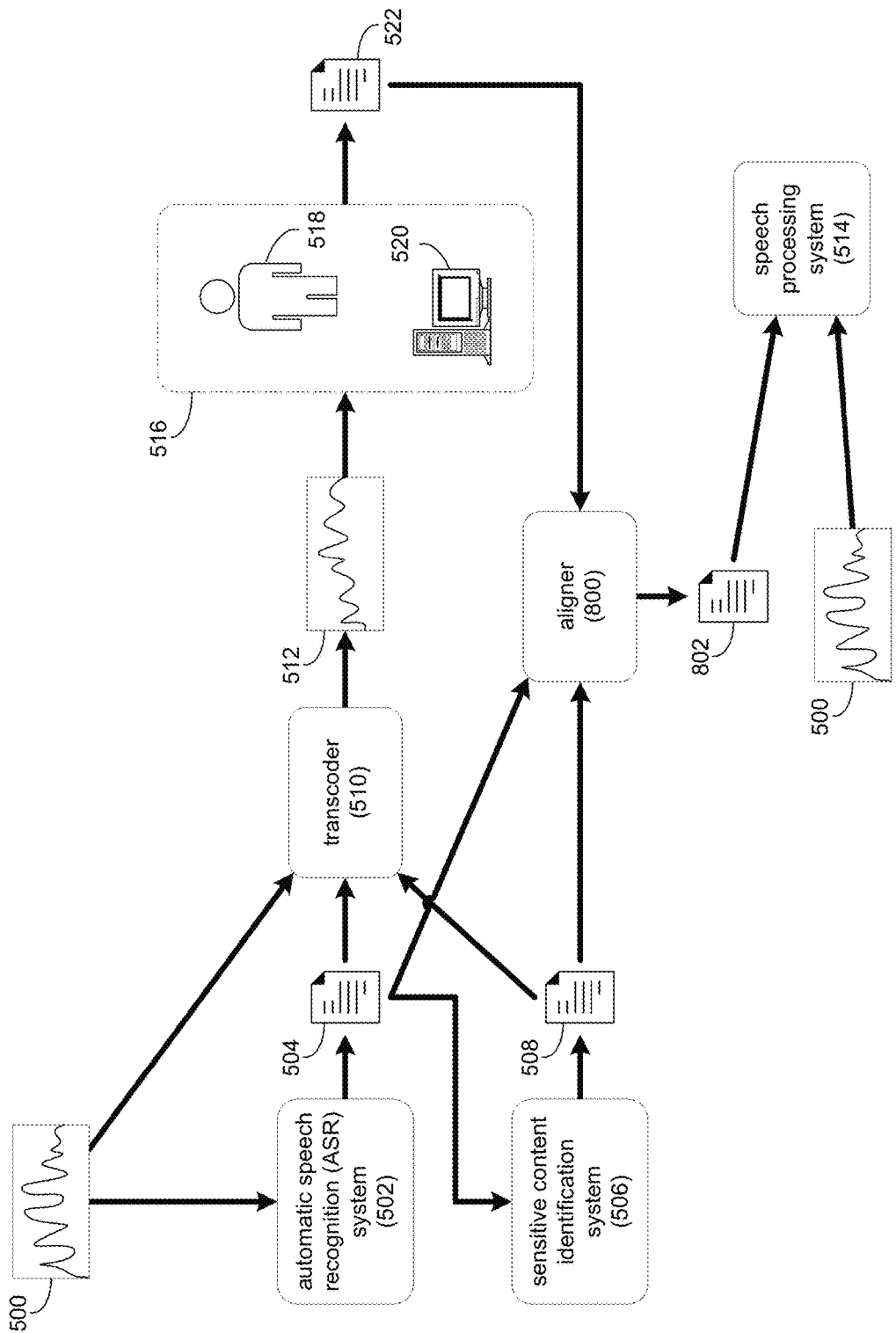
FIGS. 8-9 are diagrammatic views of the transcription generation process of FIG. 1.

In some implementations, transcription generation process 10 may receive 400 an input speech signal. For example and as discussed above, an audio recording system (e.g., audio recording system 104) may receive and record an input speech signal. Referring also to FIG. 5, transcription generation process 10 may receive 400 an input speech signal (e.g., input speech signal 500). In one example, input speech signal 500 may be received and recorded by an audio recording system (e.g., audio recording system 104) and/or may be a previously recorded audio input signal (e.g., an audio signal stored in a database or other data structure). In one example, suppose that input speech signal 500 concerns a medical encounter between a medical professional (e.g., participant 226) and a patient (e.g., participant 228). In this example, the patient (e.g., participant 228) may be asked by the medical professional (e.g., participant 226) to audibly confirm personal identification information (e.g., name, date of birth, marital status, etc.) during a medical examination. Additionally, the patient (e.g., participant 228) may describe personal health information (e.g., symptoms, medical history, etc.). Accordingly, input speech signal 500 may include sensitive content.

In some implementations, transcription generation process 10 may receive 402 a transcription of the input speech signal. For example, transcription generation process may provide the input speech signal (e.g., input speech signal 500) to an automatic speech recognition (ASR) system (e.g., ASR system 502) to generate a transcription (e.g., transcription 504) of the input speech signal (e.g., input speech signal 500). As is known in the art, automated speech recognition systems may convert input speech signals to output text. Accordingly, ASR system 502 may automatically generate transcription 504 of input speech signal 500. As will be discussed in greater detail below, transcription 504 may include any sensitive content information recorded in input speech signal 500.

In some implementations, transcription generation process 10 may identify 404 one or more sensitive content portions from the transcription of the input speech signal. Sensitive content portions may generally include any pieces or types of information that are personal, private, or subject to confidentiality. For example, the one or more sensitive content portions may include one or more of: personally identifiable information (PII) and protected health information (PHI). In addition to PII and PHI, sensitive content portions may include financial information, intellectual property, trade secrets, and/or information declared private by law or regulation. Accordingly, it will be appreciated that transcription generation process 10 may identify 404 various types of information as sensitive content within the scope of the present disclosure.

For example, transcription generation process 10 may utilize a sensitive content identification system (e.g., sensitive content identification system 506) to identify one or more sensitive content portions within the transcription (e.g., transcription 504). Sensitive content identification system 506 may include various known components such as natural language understanding (NLU) systems, artificial intelligence/machine learning models, predefined detection rules, etc. for identifying 404 one or more sensitive content portions from within the transcription. Transcription generation process 10 may provide a user interface, database, and/or other data structure of examples and/or rules for identifying sensitive content within a transcription.

Referring also to FIG. 6, consider the example transcription 504 generated from input speech signal 500 for a dialogue between "Doctor Jones" and "Patient James". In this example, transcription generation process 10 may identify 404 one or more sensitive content portions from transcription 504. For example, transcription generation process 10 may identify 404 the names "James" and "Jones"; the patient's full name "James Alan Alexander"; the patient's date of birth "Oct. 12, 1987"; the patient's medical history with migraines; and a prescription and dosage "Migraineazone four times a day". While several examples of sensitive content portions have been described, it will be appreciated that these are for example purposes only and that any number of and/or type of predefined sensitive content portions may be identified within the scope of the present disclosure.

In some implementations, transcription generation process 10 may obscure 406 the one or more sensitive content portions from the transcription of the input speech signal, thus defining an obscured transcription of the input speech signal. Obscuring 406 the one or more sensitive content portions from the transcription may generally include replacing, modifying, and/or removing the sensitive content portions from the transcription. For example, transcription generation process 10 may utilize various known components such as natural language understanding (NLU) systems, artificial intelligence/machine learning models, pre-defined detection rules, etc. for obscuring (i.e., substituting and/or removing) particular portions of sensitive content. Obscuring 406 the one or more sensitive content portions from the transcription may include changing personally identifiable information (PII) and/or protected health information (PHI). For example, transcription generation process 10 may include rules for replacing particular types of sensitive content with similar types of content. In this manner, transcription generation process 10 may obscure 406 sensitive content particular to individuals associated with a particular input speech signal.

Referring also to FIG. 7, suppose that transcription generation process 10 identifies 404 the above-mentioned sensitive content portions from transcription 504 (as shown in bold typeface in FIG. 6). In this example, transcription generation process 10 may obscure 406 the doctor's name (e.g., replacing "Jones" with "James") and the patient's name (e.g., replacing "James Alan Alexander" with "Jason Aaron Alexander"); the patient's date of birth (e.g., replacing "Oct. 12, 1987" with "Nov. 12, 1997"); and/or the patient's medical history/prescription dosage information (e.g., replacing the dosage of "Migraineazone four times a day" with "Migraineazone two times a day"). Transcription generation process 10 may output these obscured sensitive data portions in the form of an obscured transcription (e.g., obscured transcription 508). While several examples of obscuring 406 sensitive content portions has been described above, it will be appreciated that any combination of sensitive content portions may be obscured 406 by transcription generation process 10 within the scope of the present disclosure.

In some implementations, transcription generation process 10 may generate 408 an obscured speech signal based upon, at least in part, the input speech signal and the obscured transcription of the input speech signal. In some implementations, the obscured speech signal may be generated using a transcoder. Conventional transcoding approaches convert the properties (i.e., bit rate, encoding style, etc.) of a signal from one encoding format to a target encoding format. However, as used herein, transcoding by a transcoder may generally include changing the apparent "voice" and content of an input speech signal by transmuting speech content and/or speech signal properties. In this manner, transcoding, as used herein, merges two available speech processing techniques: text-to-speech (TTS) and voice transformation (e.g., to hide the speaker identity information) to modify the speaker's voice and the content of the input speech signal. Conventional approaches to generating secure transcriptions fail to generate speech signals that account for obscured sensitive content from speech signals or transcriptions.

Accordingly, transcription generation process 10 may generate 408 an obscured speech signal that creates speech content for modified portions of the obscured transcription relative to the original transcription. Example transcoder architectures/models may include Parrotron and Tacotron. As is known in the art, Parrotron is configured to perform speech to speech transformations while Tacotron is configured to perform text to speech transformations. Each of these example transcoder architectures/models include an encoder-decoder architecture that maps inputs (e.g., text in the case of Tacotron and log mel frequency representations of a speech signal in the case of Parrotron) into an encoder state and a decoder to translate the input to speech. While the examples of Parrotron and Tacotron have been provided for portions of the transcoder architecture/model, it will be appreciated that any transcoder architecture/model may be utilized within the scope of the present disclosure. Additionally/alternatively, the obscured speech signal may be generated using a text-to-speech (TTS) system configured to convert the transcription of the input speech signal into the obscured speech signal.

Generating 408 an obscured speech signal based upon, at least in part, the input speech signal and the obscured transcription of the input speech signal may include identifying 410 the one or more sensitive content portions obscured in the obscured transcription of the input speech signal, thus defining one or more obscured sensitive content portions. For example, when obscuring the one or more sensitive content portions, transcription generation process 10 may maintain a database, record, or log of obscured portions. In this manner, transcription generation process 10 may identify each sensitive content portion to synthesize for the obscured speech signal.

Generating 408 an obscured speech signal based upon, at least in part, the input speech signal and the obscured transcription of the input speech signal may include synthesizing 412 the obscured sensitive content portions to generate the obscured speech signal. For example, transcription generation process 10 may identify the sensitive content portions that are obscured in the obscured transcription. Accordingly, transcription generation process 10 may synthesize 412 the obscured sensitive content portions to generate the obscured speech signal. Synthesizing 412 the corresponding portions of the obscured transcription may generally include generating (e.g., via a speech-to-text functionality of the transcoder) speech output based on the corresponding portions of the obscured transcription. In this manner, a subsequent listener to the obscured speech signal may hear a consistent speech signal despite portions of the original speech signal being obscured.

Generating 408 an obscured speech signal based upon, at least in part, the input speech signal and the obscured transcription of the input speech signal may include comparing 414 portions of the transcription of the input speech signal to corresponding portions of the obscured transcription of the input speech signal. For example, transcription generation process 10 may configure the transcoder (e.g., transcoder 510) to modify the input speech signal (e.g., input speech signal 500) to generate the obscured speech signal for unobscured portions and to synthesize the modified portions of the obscured transcription to generate the obscured speech signal for modified portions. While FIG. 5 shows a transcoder (e.g., transcoder 510), it will be appreciated that this is for example purposes only and that various systems (e.g., text-to-speech systems) may be utilized to generate the obscured speech signal within the scope of the present disclosure. Transcription generation process 10 may compare 414 each portion (e.g., each character, word, sentence, paragraph, etc.) of the transcription of the input speech signal to corresponding portions of the obscured transcription of the input speech signal. While examples of various granularities for comparing the transcriptions have been described, it will be appreciated that transcription generation process 10 may sequentially process and compare the transcriptions at any granularity within the scope of the present disclosure.

Comparing 414 the portions of the transcription of the input speech signal to corresponding portions of the obscured transcription of the input speech signal may include determining whether the portions of the transcription of the input speech signal are the same as the corresponding portions of the obscured transcription of the input speech signal. Referring again to FIGS. 6-7, transcription generation process 10 may iteratively and sequentially compare each portion of transcription 504 with each corresponding portion of obscured transcription 508 to determine whether each portion. For example, transcription generation process 10 may compare 414 each word, sentence, and/or paragraph of transcription 504 as shown in FIG. 6 with each word, sentence, and/or paragraph of obscured transcription 508 as shown in FIG. 7.

In response to determining that the portions of the transcription of the input speech signal are different from the corresponding portions of the obscured transcription of the input speech signal, transcription generation process 10 may synthesize 416 the corresponding portions of the obscured transcription of the input speech signal to generate the obscured speech signal. For example, transcription generation process 10 may identify portions of obscured transcription 508 that do not match corresponding portions of transcription 504. Accordingly, transcription generation process 10 may, via transcoder 510, synthesize 416 the corresponding portions of the obscured transcription into portions of the obscured speech signal. Synthesizing 416 the corresponding portions of the obscured transcription may generally include generating (e.g., via a speech-to-text functionality of the transcoder) speech output based on the corresponding portions of the obscured transcription. In this manner, a subsequent listener to the obscured speech signal may hear a consistent speech signal despite portions of the original speech signal being obscured.

In response to determining that the portions of the transcription of the input speech signal are the same as the corresponding portions of the obscured transcription of the input speech signal, transcription generation process 10 may use 418 a corresponding portion of the input speech signal to generate the obscured speech signal. For example, transcription generation process 10 may use 418 speech-to-speech functionality of transcoder 510 to convert portions of the input speech signal to the same output type for unobscured portions as for obscured portions. In this manner, the obscured speech signal (e.g., obscured speech signal 512) may be audibly consistent despite portions of the input speech signal being obscured in the obscured transcription. As will be discussed in greater detail below, by having consistent audible characteristics in the obscured speech signal, a speech processing system (e.g., speech processing system 514) may be more accurately trained to process input speech for a target output text. In some implementations, as opposed to using the original input speech signal, the transcription of the input speech signal may be processed with a text-to-speech system such that the resulting version of the input speech signal will not be based on the original input signal. In this manner, the original input speech signal may be insulated from use in a manner that may expose sensitive content.

Generating 408 an obscured speech signal based upon, at least in part, the input speech signal, the transcription of the input speech signal, and the obscured transcription of the input speech signal may include modifying 420 one or more properties of the input speech signal to disguise personal identification information within the input speech signal. For example and as discussed above, one of the regulatory challenges associated with speech signals is the risk of being able to identify a speaker's identity based on sufficiently long recordings of the speaker's voice. For instance, suppose input speech signal 500 includes a conversation between a patient and a medical professional but the medical professional never says his or her name. Despite the lack of personally identifiable information in the content of the conversation, the speaker's voice characteristics may allow the speaker to be identifiable.

Accordingly, transcription generation process 10 may perform various speech signal modifications on the input speech signal, via the transcoder (e.g., transcoder 510) to reduce the likelihood that a speaker's voice may be personally identifiable. For example, transcription generation process 10 may modify 420 the gain, noise, reverberation, cadence, speed, or other properties of the input speech signal (or particular portions (i.e., time segments, target frequencies, etc.)) to avoid retaining personally identifiable information. In this manner, transcription generation process 10 may obscure content-based sensitive information and spectrally sensitive information from the input speech signal (e.g., input speech signal 500). Additionally/alternatively and as discussed above, the transcription of the input speech signal may be processed with a text-to-speech system such that the resulting version of the input speech signal will not be based on the original input signal. In this manner, the original input speech signal may be insulated from use in a manner that may expose sensitive content. Accordingly, transcription generation process may perform various speech signal modifications on the revised version of the input speech signal, via the transcoder (e.g., transcoder 510) to reduce the likelihood that a speaker's voice may be personally identifiable.

In some implementations, transcription generation process 10 may receive 422 a manually generated transcription of the obscured speech signal. For example, transcription generation process 10 may provide the obscured speech signal (e.g., obscured speech signal 512) to a transcriber (e.g., transcriber 516) to generate a manually generated transcription of the obscured speech signal. As discussed above, transcription generation process 10 may utilize collected speech signals (e.g., input speech signal 500) to improve speech processing system (e.g., speech processing system 514) accuracy by training the speech processing system with labeled data (i.e., input speech data and corresponding textual data, in the case of speech-to-text processing). Accordingly, transcription generation process 10 may provide the obscured speech signal (e.g., obscured speech signal 512) to a transcriber (e.g., transcriber 516) to generate a transcription of the obscured speech signal. A transcriber (e.g., transcriber 516) may generally include a human (e.g., user 518) utilizing a software system and/or a hybrid approach including a speech processing system (e.g., another ASR system 520). Accordingly, it will be appreciated that transcriber 516 may include any group of users and/or software models configured to process and label obscured speech signal 512.

As discussed above, by generating obscured speech signal 512, transcription generation process 10 may obscure 406 and/or modify 420 input speech signal 500 in such a way as to remove or reduce the likelihood of sensitive information being shared with transcriber 516. As shown in FIG. 5, transcription generation process 10 may receive 422, from transcriber 516, a transcription of the obscured speech signal (e.g., transcription 522). As discussed above, transcription 522 may include a labeling of the content of input speech signal 512 for use in training a speech processing system (e.g., speech processing system 514).

In some implementations, transcription generation process 10 may train 424 a speech processing model based upon, at least in part, the manually generated transcription of the obscured speech signal. As discussed above, training 424 a speech processing system (e.g., speech processing system 514) may include providing labeled data and input speech data for the speech processing system to "learn" from. For example and as is known in the art, machine learning generally includes the training of an algorithm or combination of to recognize certain types of patterns. Machine learning approaches may be generally divided into three categories, depending on the nature of the signal available: supervised learning, unsupervised learning, and reinforcement learning. As is known in the art, supervised learning may include presenting a computing device with example inputs and their desired outputs, given by a "teacher", where the goal is to learn a general rule that maps inputs to outputs. With unsupervised learning, no labels are given to the learning algorithm, leaving it on its own to find structure in its input. Unsupervised learning can be a goal in itself (discovering hidden patterns in data) or a means towards an end (feature learning). As is known in the art, reinforcement learning may generally include a computing device interacting in a dynamic environment in which it must perform a certain goal (such as driving a vehicle or playing a game against an opponent). As it navigates its problem space, the program is provided feedback that's analogous to rewards, which it tries to maximize. While three examples of machine learning approaches have been provided, it will be appreciated that other machine learning approaches are possible within the scope of the present disclosure.

Training 424 the speech processing model based upon, at least in part, the manually generated transcription of the obscured speech signal may include training 426 the speech processing model based upon, at least in part, the manually generated transcription of the obscured speech signal and the obscured speech signal. In this example, transcription generation process 10 may train 426 the speech processing system (e.g., speech processing system 514) with the combination of the obscured speech signal (e.g., obscured speech signal 512) and the manually generated transcription of the obscured speech signal (e.g., manually generated transcription 522). Accordingly, manually generated transcription 522 may act as labeled data for the obscured speech signal. This approach may also allow for the original input speech signal (e.g., input speech signal 500) to be discarded. In this manner, transcription generation process 10 may utilize an input speech signal originally containing sensitive content portions to be utilized for training data without disclosing the sensitive content to external parties. Additionally, by discarding of the original input speech signal, data privacy requirements may be reduced or avoided altogether.

Training 424 the speech processing model based upon, at least in part, the manually generated transcription of the obscured speech signal may include aligning 428 the manually generated transcription of the obscured speech signal with the transcription of the input speech signal; and incorporating 430 the one or more sensitive content portions into the manually generated transcription of the obscured speech signal, thus defining a modified manually generated transcription. For example and referring also to FIG. 8, it may be beneficial to utilize the labeling of the manually generated transcription of the obscured speech signal with the content of the original input speech signal. Accordingly, transcription generation process 10 may align 428, via aligner 800, the manually generated transcription of the obscured speech signal (e.g., manually generated transcription 522) with the transcription of the input speech signal (e.g., transcription 504). Aligning 428 the manually generated transcription of the obscured speech signal with the transcription may generally include identifying corresponding portions from each transcription to synchronize the transcriptions. In this manner, transcription generation process 10 may generate a mixed automatic and manual transcription of the input speech signal.

With the manually generated transcription of the obscured speech signal (e.g., manually generated transcription 522) aligned with the transcription of the input speech signal (e.g., transcription 504), transcription generation process 10 may incorporate 430 the one or more sensitive content portions into the manually generated transcription of the obscured speech signal (e.g., manually generated transcription 522) to generate the modified manually generated transcription (e.g., modified manually generated transcription 802). In this manner, transcription generation process 10 may reintroduce the sensitive content portions into the manually generated transcription to allow a speech processing system (e.g., speech processing system 514) to be trained using the original input speech signal (e.g., input speech signal 500) and the modified manually generated transcription (e.g., modified manually generated transcription 802). Accordingly, transcription generation process 10 may provide the modified manually generated transcription (e.g., modified manually generated transcription 802) and the input speech signal (e.g., input speech signal 500) as training data to speech processing system 514.

Figure 9:
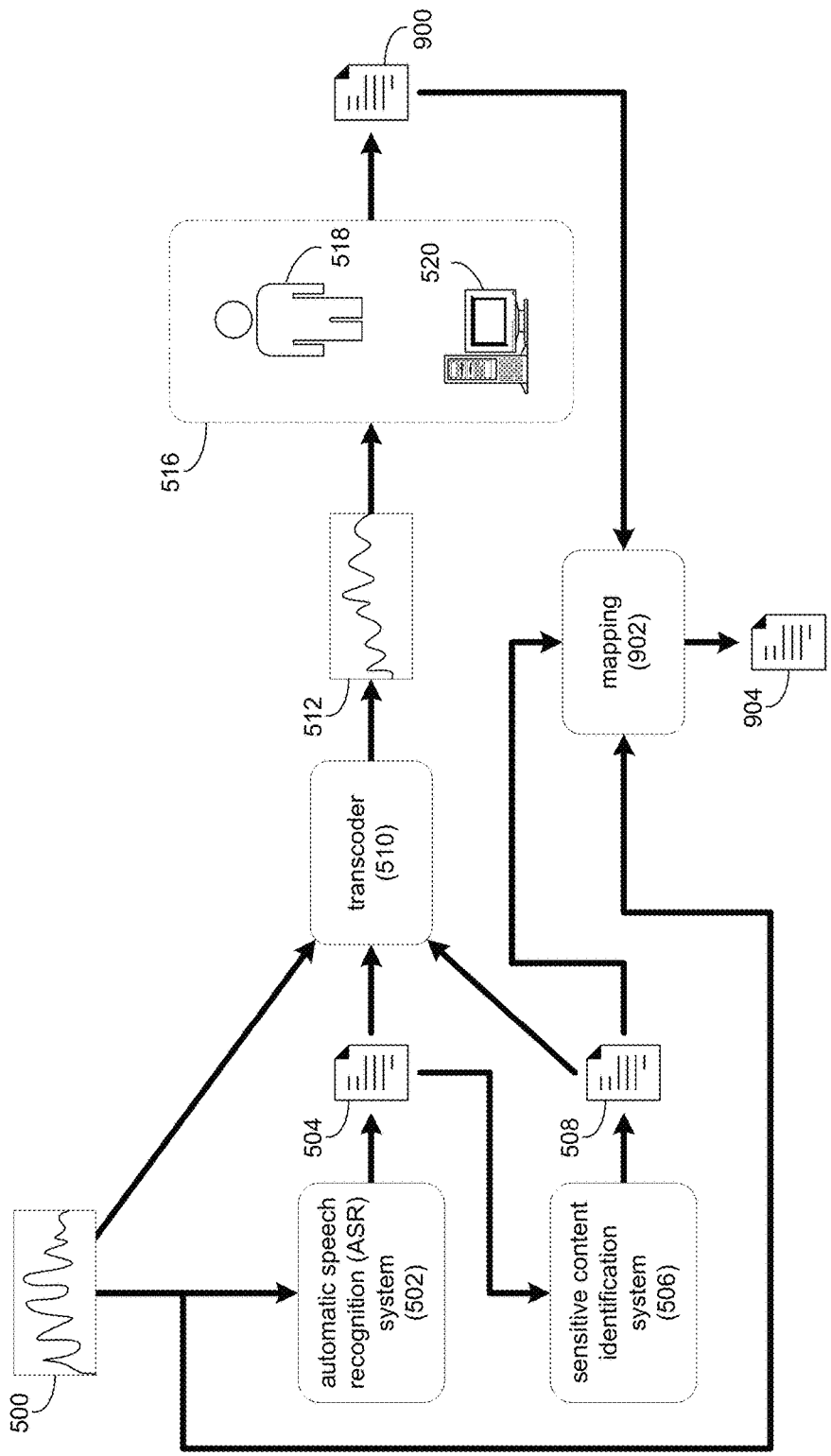

In some implementations, transcription generation process 10 may allow for the generation of reports (i.e., medical reports from medical encounter transcriptions and/or various reports for particular encounter transcriptions) while limiting the exposure of sensitive content from other users (e.g., scribes). Referring also to FIG. 9 and comparing to FIG. 5, transcriber 516 may generate an obscured report (e.g., obscured report 900) from the obscured speech signal (e.g., obscured speech signal 512). However, as obscured report 900 does not include sensitive content, transcription process 10 may utilize a mapping between the ASR input and the output of sensitive content identification system 506 to map sensitive content to the obscured data in the obscured report (e.g., obscured report 900). Mapping 902 may represent one or more mappings generated between input speech signal 500 and the output of sensitive content identification system 506. Mapping 902 may be a predefined mapping that is user-defined and/or may be automatically and dynamically defined by transcription generation process 10 using one or more machine learning models based in the ASR input and the output of sensitive content identification system 506. In this manner, transcription generation process 10 may utilize the ASR input (e.g., input speech signal 500), the obscured report 900, and mapping 902 to generate a complete report including the sensitive content (e.g., complete report 904).

Figure 10:
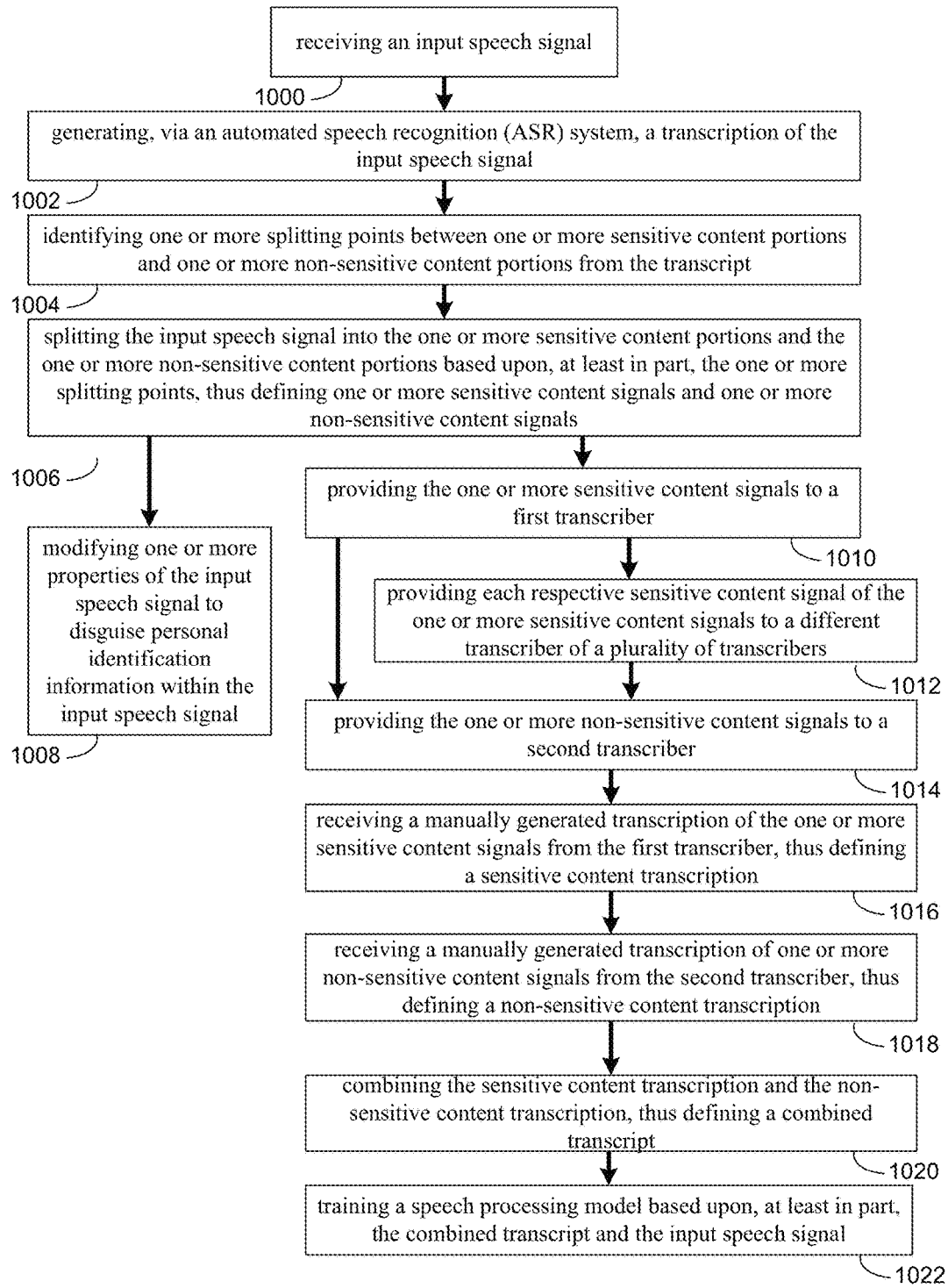
FIG. 10 is a flow chart of one implementation of the transcription generation process of FIG. 1.
Figure 11:
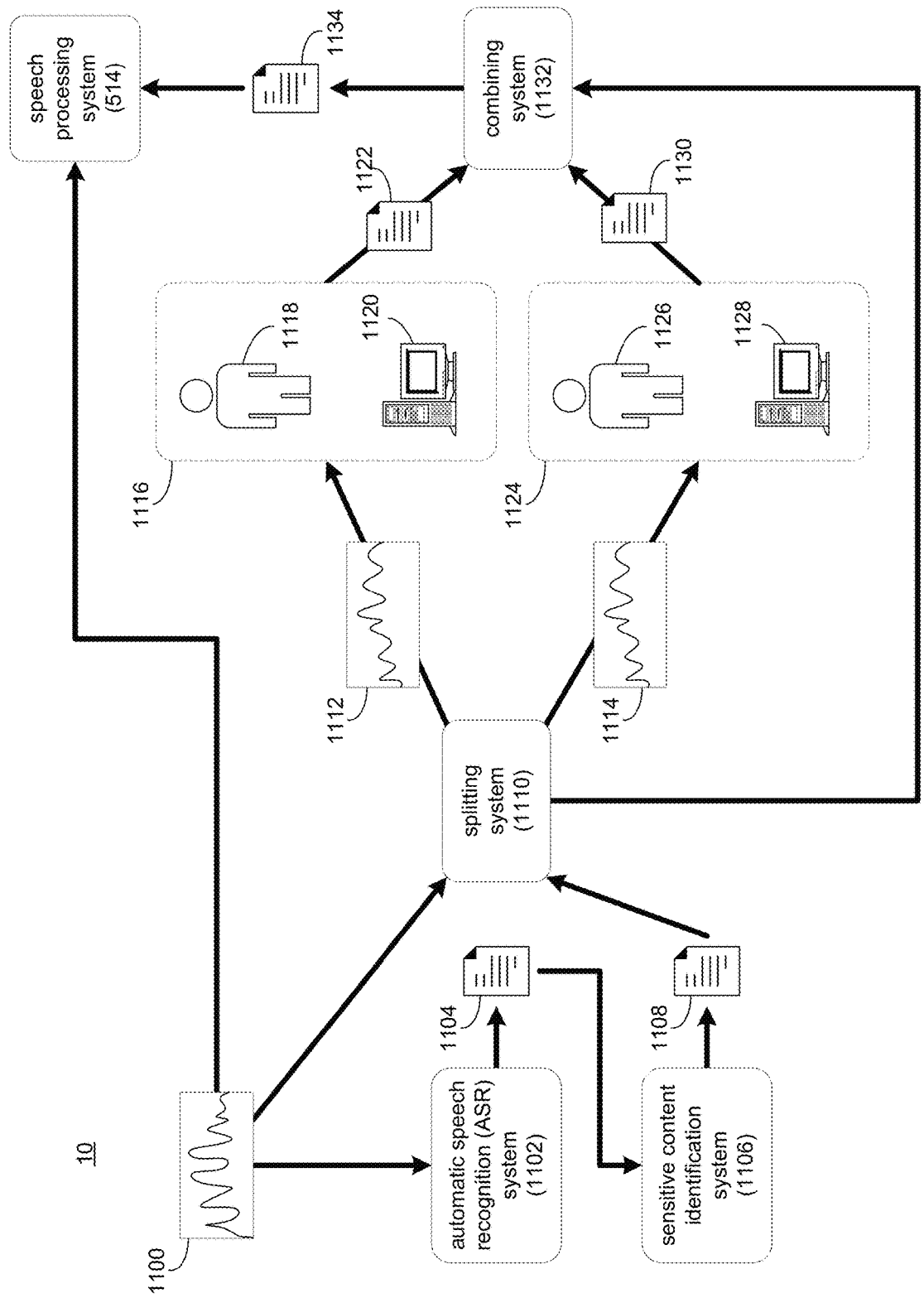
FIG. 11 is a diagrammatic view of the transcription generation process of FIG. 1.

Referring also at least to FIGS. 10-11, transcription generation process 10 may receive 1000 an input speech signal. A transcription of the input speech signal may be generated 1002 via an automated speech recognition (ASR) system. One or more splitting points between one or more sensitive content portions and one or more non-sensitive content portions from the transcription may be identified 1004. The input speech signal maybe split 1006 into the one or more sensitive content portions and the one or more non-sensitive content portions based upon, at least in part, the one or more splitting points, thus defining one or more sensitive content signals and one or more non-sensitive content signals.

In some implementations consistent with the present disclosure, systems and methods may be provided for generating transcriptions without exposing sensitive content from within input speech signals. For example and as will be discussed in greater detail below, ASR and NLU can be used to identify sensitive content from an input speech signal (e.g., patient names and medical record numbers). The speech signal may be segmented into different audios for transcription, which would be sent to different transcribers. One audio may include the sensitive content (and a few seconds of 'buffer' before and after each snippet) and the other audio may include the rest of the original input speech signal. These audios may be sent to different transcribers, so that neither transcriber could breach the whole conversation. This measure may result in less damaging breaches of sensitive content and may make any stored speech data less attractive to a potential breacher.

In some implementations, transcription generation process 10 may receive 1000 an input speech signal. For example and as discussed above, an audio recording system (e.g., audio recording system 104) may receive and record an input speech signal. Referring also to FIG. 11, transcription generation process 10 may receive 1000 an input speech signal (e.g., input speech signal 1100). In one example, input speech signal 1000 may be received and recorded by an audio recording system (e.g., audio recording system 104) and/or may be a previously recorded audio input signal (e.g., an audio signal stored in a database or other data structure). In one example, suppose that input speech signal 1100 concerns a medical encounter between a medical professional (e.g., participant 226) and a patient (e.g., participant 228). In this example, the patient (e.g., participant 228) may be asked by the medical professional (e.g., participant 226) to audibly confirm personal identification information (e.g., name, date of birth, marital status, etc.) during a medical examination. Additionally, the patient (e.g., participant 228) may describe personal health information (e.g., symptoms, medical history, etc.). Accordingly, input speech signal 1100 may include sensitive content information.

Transcription generation process 10 may generate 1002, via an automated speech recognition (ASR) system, a transcription of the input speech signal. For example, transcription generation process 10 may provide the input speech signal (e.g., input speech signal 1100) to an automatic speech recognition (ASR) system (e.g., ASR system 1102) to generate a transcription (e.g., transcription 1104) of the input speech signal (e.g., input speech signal 1100). As is known in the art, automated speech recognition systems may convert input speech signals to output text. Accordingly, ASR system 1002 may automatically generate transcription 1104 of input speech signal 1100. As will be discussed in greater detail below, transcription 1104 may include any sensitive content information recorded in input speech signal 1100.

In some implementations, transcription generation process 10 may identify 1004 one or more splitting points between one or more sensitive content portions and one or more non-sensitive content portions from the transcription. For example and as discussed above, transcription generation process 10 may identify one or more sensitive content portions from the transcription of the input speech signal. Sensitive content portions may generally include any pieces or types of information that are personal, private, or subject to confidentiality. For example, the one or more sensitive content portions may include one or more of: personally identifiable information (PII) and protected health information (PHI). In addition to PII and PHI, sensitive content portions may include financial information, intellectual property, trade secrets, and/or information declared private by law or regulation. Accordingly, it will be appreciated that transcription generation process 10 may identify various types of information as sensitive content.

For example, transcription generation process 10 may utilize a sensitive content identification system (e.g., sensitive content identification system 1106) to identify one or more sensitive content portions within the transcription (e.g., transcription 1104). Sensitive content identification system 1106 may include various known components such as natural language understanding (NLU) systems, artificial intelligence/machine learning models, predefined detection rules, etc. for identifying 1004 one or more sensitive content portions from within the transcription. Transcription generation process 10 may provide a user interface, database, and/or other data structure of examples and/or rules for identifying sensitive content within a transcription.

Identifying 1004 one or more splitting points between one or more sensitive content portions and one or more non-sensitive content portions from the transcription may include identifying the one or more sensitive content portions within the transcription. For example and referring again to the example transcription of FIG. 6, transcription generation process 10 may identify various sensitive content portions (e.g., "James"; "Doctor Jones"; "James Alan Alexander"; "Oct. 12, 1987"; "migraines"; "Migraineazone four times a day"). Accordingly, transcription generation process 10 may identify one or more splitting points in the input speech signal for isolating the audio portions of the sensitive content portions. For example, transcription generation process 10 may identify timestamps before and after each sensitive content portion within the input speech signal corresponding to the sensitive content portions, thus defining the one or more splitting points (e.g., one or more splitting points 1108).

In some implementations, the one or more splitting points may include a predefined amount of audio before and after the one or more sensitive content portions. For example, suppose a sensitive content portion starts at e.g., 187 seconds within the input speech signal, and goes to e.g., 188.5 seconds. In this example, transcription generation process 10 may define a splitting point at e.g., 187 seconds and another splitting point at e.g., 188.5 seconds. Accordingly and as will be discussed in greater detail below, transcription generation process 10 may provide 0 to 187 seconds and 188.5 seconds to the end of the input speech signal to a non-sensitive content transcriber while providing e.g., 186 seconds to e.g., 189.5 to the sensitive content transcriber. In this manner, the non-sensitive content transcriber will not receive sensitive content while the sensitive content transcriber may receive a portion of non-sensitive context (e.g., the predefined amount of audio) to aid in their transcribing. The predefined amount of audio before and/or after the one or more sensitive content portions may be a default amount, a user-defined amount, and/or automatically defined by transcription generation process 10. In some implementations, the predefined amount of audio before and/or after the one or more sensitive content portions may be provided in the one or more non-sensitive content portions (i.e., may be duplicated to appear in both non-sensitive content portions and in sensitive content portions) rather than being absent or removed from the one or more non-sensitive content portions.

In some implementations, identifying 1004 one or more splitting points between one or more sensitive content portions and one or more non-sensitive content portions from the transcription may include identifying the one or more sensitive content portion types within the transcription. For example, transcription generation process 10 may identify 1004 sensitive content portions pertaining to unique types of sensitive content. In one example, transcription generation process 10 may identify a person's legal name; a person's medical information; financial information (i.e., bank account information); or other types of sensitive content. For example, natural language understanding (NLU) systems, artificial intelligence/machine learning models, predefined detection rules, etc. may be utilized to identify particular sensitive content portion categories. In some implementations, the one or more sensitive content portion categories may be predefined, default categories, user-defined (e.g., via a user interface), and/or algorithmically learned via a machine learning system. In this manner, transcription generation process 10 may separately identify sensitive content for different sensitive content types.

As will be discussed in greater detail below, the one or more splitting points (e.g., one or more splitting points 1108) may be utilized to identify sensitive audio portions and non-sensitive audio portions within the input speech signal (e.g., input speech signal 1100). While an example of a single category of sensitive audio portions has been described, it will be appreciated that transcription generation process 10 may identify 1004 any number of types of splitting points for splitting the input speech signal within the scope of the present disclosure.

Transcription generation process 10 may split 1006 the input speech signal into the one or more sensitive content portions and the one or more non-sensitive content portions based upon, at least in part, the one or more splitting points, thus defining one or more sensitive content signals and one or more non-sensitive content signals. For example, transcription generation process 10 may utilize a splitting system (e.g., splitting system 1110) to process the one or more splitting points (e.g., one or more splitting points 1108) to split 1006 the input speech signal (e.g., input speech signal 1100) into one or more sensitive content signals (e.g. represented by sensitive content signal 1112) including the one or more sensitive content portions and one or more non-sensitive content signals (e.g., represented by non-sensitive content signal 1114) including the one or more non-sensitive content portions. Splitting system 1110 may include any known software module(s) configured to split input audio content into a plurality of segments based on input constraints. It will be appreciated that transcription generation process 10 may split 1006 the input speech signal into any number of portions within the scope of the present disclosure. For example, various portions may be defined for varying levels of content sensitivity (e.g., low sensitivity, medium sensitivity, and/or high sensitivity).

Continuing with the above example, suppose a sensitive content portion (e.g., sensitive content signal 1112) starts at e.g., 187 seconds within input speech signal 1100, and goes to e.g., 188.5 seconds. In this example, transcription generation process 10 may define a splitting point (e.g., one or more splitting points 1108) at e.g., 187 seconds and another splitting point at e.g., 188.5 seconds. Sensitive content signal 1112 may include the portions of input speech signal 1100 corresponding to the one or more sensitive content portions identified in transcription 1104 and non-sensitive content speech signal 1114 may include the remaining portions of input speech signal 1100. Accordingly, sensitive content signal 1112 may include primarily sensitive content without the majority of the context of input speech signal 1100 while non-sensitive content speech signal 1114 may include only non-sensitive content portions of input speech signal 1100. In this manner, transcription generation process 10 may isolate sensitive content from non-sensitive content. While an example has been provided for splitting 1006 input speech signal 1100 into e.g., two speech signals, it will be appreciated that transcription generation process 10 may split input speech signal 1100 into any number of signals.

For example, transcription generation process 10 may split input speech signal 1100 into multiple speech signals based upon, at least in part, the type of sensitive content identified within transcription 1104. In one example, transcription generation process 10 may split input speech signal 1100 into a one speech signal for personally identifiable information (PII), one speech signal for protected health information (PHI), and another speech signal for all remaining content from input speech signal 1100. Accordingly, it will be appreciated that transcription generation process 10 may split the input speech signal into any number of speech signals based upon, at least in part, the one or more splitting points.

Transcription generation process 10 may modify 908 one or more properties of the input speech signal to disguise personal identification information within the input speech signal. For example and as discussed above, one of the regulatory challenges associated with speech signals is the risk of being able to identify a speaker's identity based on sufficiently long recordings of the speaker's voice. For instance, suppose input speech signal 1100 includes a conversation between a patient and a medical professional but the medical professional never says his or her name. Despite the lack of personally identifiable information in the content of the conversation, the speaker's voice characteristics may allow the speaker to be identifiable.

Accordingly, transcription generation process 10 may perform various speech signal modifications on the input speech signal to reduce the likelihood that a speaker's voice may be personally identifiable. For example, transcription generation process 10 may modify 1008 the gain, noise, reverberation, cadence, speed, or other properties of the input speech signal (or particular portions (i.e., time segments, target frequencies, etc.)) to avoid retaining personally identifiable information. In some implementations, transcription generation process 10 may utilize voice style transfer (VST) methods (i.e., audio-to-audio transformation methods that accept an input a speech segment and a target speaker embedding and output audio that sounds like the target speaker's voice). Accordingly, transcription generation process 10 may modify 1008 the input speech signal by performing a VST to a standard speaker, which would then make the speech segment PII-preserving from the speaker "voice" point of view and this could be done in addition to other processing such as modifying the pitch, etc. In this manner, transcription generation process 10 may obscure content-based sensitive information and spectrally sensitive information from the input speech signal (e.g., input speech signal 1000) while still sounding like the speaker's voice.

In some implementation, transcription generation process 10 may provide 1010 the sensitive content signal to a first transcriber. For example, transcription generation process 10 may provide the sensitive content signal (e.g., sensitive content signal 1112) to a transcriber (e.g., transcriber 1116) to generate a manually generated transcription of the sensitive content signal. As discussed above, transcription generation process 10 may utilize collected speech signals (e.g., input speech signal 1100) to improve speech processing system (e.g., speech processing system 514) accuracy by training the speech processing system with labeled data (i.e., input speech data and corresponding textual data, in the case of speech-to-text processing).

Accordingly, transcription generation process 10 may provide 1010 the sensitive content signal (e.g., sensitive content signal 1112) to a transcriber (e.g., transcriber 1116) to generate a transcription of the sensitive content signal. A transcriber (e.g., transcriber 1116) may generally include a human (e.g., user 1118) utilizing a software system and/or a hybrid approach including a speech processing system (e.g., another ASR system 1120). Accordingly, it will be appreciated that transcriber 1116 may include any group of users and/or software models configured to process and label sensitive content signal 1112. As discussed above, by generating sensitive content signal 1112, transcription generation process 10 may isolate the sensitive content of input speech signal 1100 in such a way as to remove or reduce the likelihood of revealing the entirety of input speech signal 1100. As shown in FIG. 11, transcription generation process 10 may receive 1014, from transcriber 1116, a manually generated transcription of the sensitive content signal, thus defining a sensitive content transcription (e.g., sensitive content transcription 1122). While transcriber 1116 is described as a single transcriber, it will be appreciated that this is for example purposes only and that providing 1010 the sensitive content signal (e.g., sensitive content signal 1112) to a transcriber (e.g., transcriber 1116) to generate a transcription of the sensitive content signal may include providing sensitive content signal to one or more transcribers. In some implementations, the first transcriber or first set of transcribers may include a trusted and/or closely supervised set of transcribers for receiving more sensitive content.

Providing 1010 the one or more sensitive content signals to the first transcriber may include providing 1012 each respective sensitive content signal of the one or more sensitive content signals to a different transcriber of a plurality of transcribers. For example and as discussed above, suppose transcription generation process 10 identifies multiple types of sensitive content. Transcription generation process 10 may provide 1012 these respective sensitive content signals to different transcribers. For example, one transcriber may receive personal medical information while another transcriber may receive financial information. In this manner, each transcriber may only have access to a limited portion or type of sensitive content.

In some implementations, transcription generation process 10 may provide 1014 the non-sensitive content signal to a second transcriber. For example, transcription generation process 10 may provide the non-sensitive content signal (e.g., non-sensitive content signal 1114) to a transcriber (e.g., transcriber 1124) to generate a manually generated transcription of the non-sensitive content signal. As discussed above, a transcriber (e.g., transcriber 1124) may generally include a human (e.g., user 1126) utilizing a software system and/or a hybrid approach including a speech processing system (e.g., another ASR system 1128). Accordingly, it will be appreciated that transcriber 1124 may include any group of users and/or software models configured to process and label non-sensitive content signal 1114. In some implementations, second transcriber 1124 may include a transcriber with a different set of authorizations or permissions to access and transcribe sensitive material than that of the first transcriber (e.g., first transcriber 1116). For example, the first transcriber (e.g., transcriber 1116) may include the most trusted and/or most closely supervised transcribers for receiving more sensitive content while non-sensitive content may be transcribed by the second transcriber (e.g., transcriber 1124) who is less supervised and/or in a less secure environment (e.g., contractors working from home). In this manner, the distinction between first transcribers who receive sensitive content and second transcribers who receive non-sensitive content may be based upon, at least in part, the degree of data security and varying levels of trust or data security training of the transcribers. As discussed above, by generating non-sensitive content signal 1114, transcription generation process 10 may remove the sensitive content of input speech signal 1100 in such a way as to remove or reduce the likelihood of revealing the entirety of input speech signal 1100. As shown in FIG. 11, transcription generation process 10 may receive 1018, from transcriber 1124, a manually generated transcription of the non-sensitive content signal from the second transcriber, thus defining a non-sensitive content transcription (e.g., non-sensitive content transcription 1130).

While the above examples include two transcribers, it will be appreciated that any number of transcribers may receive speech signals and generate transcriptions of their respective portions. For example, transcription generation process 10 may provide the same transcriber (e.g., transcriber 1116) with both speech signals (e.g., sensitive content signal 1112 and non-sensitive content signal 1114) but at different times. In this example, transcription generation process 10 may provide sensitive content signal 1112 to transcriber 1116. After a predefined amount of time, transcription generation process 10 may provide non-sensitive content signal 1114 to transcriber 1116. In this manner, transcriber 1116 may generate transcriptions for both signals without being aware of their connection. As such, transcription generation process 10 may reduce the number of transcribers required to transcribe sensitive content within an input speech signal by providing the speech signal separately over time. In some implementations, the amount of time defined between providing each speech signal may be user-defined (e.g., via a user interface), may be automatically defined by transcription generation process 10, and/or may be a default value (e.g., three days). Accordingly, it will be appreciated that transcription generation process may provide the segmented speech signals to the same transcriber after any period of time within the scope of the present disclosure.

Continuing with the above example, transcription generation process 10 may provide 0 to 187 seconds and 188.5 seconds to the end of the input speech signal (e.g., non-sensitive content signal 1114) to a non-sensitive content transcriber (e.g., transcriber 1124) while providing e.g., 186 seconds to e.g., 189.5 seconds (e.g., sensitive content signal 1112) to the sensitive content transcriber (e.g., transcriber 1116). In this manner, the non-sensitive content transcriber (e.g., transcriber 1124) will not receive sensitive content (e.g., non-sensitive content signal 1114) while the sensitive content transcriber (e.g., transcriber 1116) may receive a portion of non-sensitive context (e.g., the predefined amount of audio) to aid in their transcribing.

In some implementations, transcription generation process 10 may combine 1020 the sensitive content transcription and the non-sensitive content transcription, thus defining a combined transcription. For example, sensitive content transcription 1122 may include sensitive content from input speech signal 1100 while non-sensitive content transcription 1130 may include all other portions of input speech signal 1100. Accordingly, transcription generation process 10 may combine 1020, using combining system 1132, the sensitive content transcription 1122 and non-sensitive content transcription 1130 to form a combined transcription (e.g., combined transcription 1134) representative of all of the content (i.e., sensitive and non-sensitive portions) of input speech signal 1100. Combining system 1132 may be any known software module(s) configured to combine separate transcriptions using a reference audio input (e.g., input speech signal 1100). In some implementations and as shown in FIG. 11, combining system 1132 may receive an input for synchronizing the sensitive content transcription 1122 and non-sensitive content transcription 1130 to form a combined transcription (e.g., combined transcription 1134) representative of the content (i.e., sensitive and non-sensitive portions) of input speech signal 1100.

For example, transcription generation process 10 may provide a synchronization/splitting signal from splitting system 1110 to combining system 1132 (represented in FIG. 11 as the line from splitting system 1110 to combining system 1132). In this manner, transcription generation process 10 may utilize the splitting signal or information from splitting system 1110 to synchronize sensitive content transcription 1122 and non-sensitive content transcription 1130 when generating combined transcription 1134. While the splitting signal/information is shown as a direct link between splitting system 1110 and combining system 1132, it will be appreciated that transcription generation process 10 may provide splitting signal/information from splitting system 1110 through one or more intervening systems or processes. Additionally and/or alternatively, transcription generation process 10 may provide information embedded in one or more of the sensitive content transcription 1122 and non-sensitive content transcription 1130 to combining system 1132 to allow combining system 1132 to synchronize sensitive content transcription 1122 and non-sensitive content transcription 1130.

Transcription generation process 10 may train 1022 a speech processing model based upon, at least in part, the combined transcription and the input speech signal. For example, transcription generation process 10 may train 1022 the speech processing system (e.g., speech processing system 514) with the combination of the input speech signal (e.g., obscured speech signal 1100) and the combined transcription (e.g., combined transcription 1134). Accordingly, combined transcription 1134 may act as labeled data for the input speech signal. This approach may allow for the labeling of the input speech signal (e.g., input speech signal 1100) with a reduced likelihood of exposing all of input speech signal to a particular transcriber. In this manner, transcription generation process 10 may utilize an input speech signal originally containing sensitive content portions for training data without disclosing the sensitive content or all of the content to external parties.

In some implementations, transcription generation process 10 may selectively remove sensitive content from the training of a speech processing system. For example, some or all of sensitive content may be identified as noted above but instead of providing the sensitive content for transcription, transcription generation process 10 may dispose of the one or more sensitive content signals (e.g., sensitive content signals 1112). In this manner, a speech processing system (e.g., speech processing system 514) may be trained using only non-sensitive content from the input speech signal.

General

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, not at all, or in any combination with any other flowcharts depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:
   receiving an input speech signal by utilizing one or more of a plurality of discrete audio acquisition devices to form an audio recording beam, thus enabling capturing of the input speech signal produced by an encounter participant as at least one audio acquisition device is directed toward the encounter participant;
   generating, via an automated speech recognition (ASR) system, a transcription of the input speech signal;
   identifying one or more splitting points between one or more sensitive content portions and one or more non-sensitive content portions from the transcription;
   splitting the input speech signal into the one or more sensitive content portions and the one or more non-sensitive content portions utilizing a splitting system based upon, at least in part, the one or more splitting points, thus defining one or more sensitive content signals and one or more non-sensitive content signals;
   processing a transcription of the one or more sensitive content signals generated by a first transcriber, thus defining a sensitive content transcription;
   processing a transcription of the one or more non-sensitive content signals generated by a second transcriber, thus defining a non-sensitive content transcription;
   generating a combined transcription by combining the sensitive content transcription and the non-sensitive content transcription and by utilizing a splitting signal from the splitting system to synchronize the sensitive content transcription and the non-sensitive content transcription when generating the combined transcription;
   training a speech processing model based upon, at least in part, the combined transcription and the input speech signal originally containing the one or more sensitive content portions for training data, wherein the combined transcription acts as labeled data for the input speech signal without disclosing all of the input speech signal to either the first transcriber or the second transcriber; and
   processing speech input using the trained speech processing model.

2. The computer-implemented method of claim 1, wherein the one or more sensitive content portions include one or more of:
   personally identifiable information (PII); and
   protected health information (PHI).

3. The computer-implemented method of claim 1, further comprising:
   modifying one or more properties of the input speech signal to disguise personal identification information within the input speech signal.

4. The computer-implemented method of claim 1, further comprising:
   providing the one or more sensitive content signals to the first transcriber.

5. The computer-implemented method of claim 4, wherein providing the one or more sensitive content signals to the first transcriber includes providing each respective sensitive content signal of the one or more sensitive content signals to a different transcriber of a plurality of transcribers.

6. The computer-implemented method of claim 4, further comprising:
providing the one or more non-sensitive content signals to the second transcriber.

7. A computer program product residing on a non-transitory computer readable medium having a plurality of instructions stored thereon which, when executed by a processor, cause the processor to perform operations comprising:
receiving an input speech signal by utilizing one or more of a plurality of discrete audio acquisition devices to form an audio recording beam, thus enabling capturing of the input speech signal produced by an encounter participant as at least one audio acquisition device is directed toward the encounter participant;
generating, via an automated speech recognition (ASR) system, a transcription of the input speech signal;
identifying one or more splitting points between one or more sensitive content portions and one or more non-sensitive content portions from the transcript;
splitting the input speech signal into the one or more sensitive content portions and the one or more non-sensitive content portions utilizing a splitting system based upon, at least in part, the one or more splitting points, thus defining one or more sensitive content signals and one or more non-sensitive content signals;
processing a transcription of the one or more sensitive content signals generated by a first transcriber, thus defining a sensitive content transcription;
processing a transcription of the one or more non-sensitive content signals generated by a second transcriber, thus defining a non-sensitive content transcription;
generating a combined transcription by combining the sensitive content transcription and the non-sensitive content transcription and by utilizing a splitting signal from the splitting system to synchronize the sensitive content transcription and the non-sensitive content transcription when generating the combined transcription;
training a speech processing model based upon, at least in part, the combined transcription and the input speech signal originally containing the one or more sensitive content portions for training data, wherein the combined transcription acts as labeled data for the input speech signal without disclosing all of the input speech signal to either the first transcriber or the second transcriber; and
processing speech input using the trained speech processing model.

8. The computer program product of claim 7, wherein the one or more sensitive content portions include one or more of:
personally identifiable information (PII); and
protected health information (PHI).

9. The computer program product of claim 7, wherein the operations further comprise:
modifying one or more properties of the input speech signal to disguise personal identification information within the input speech signal.

10. The computer program product of claim 7, wherein the operations further comprise:
providing the one or more sensitive content signals to the first transcriber.

11. The computer program product of claim 10, wherein providing the one or more sensitive content signals to the first transcriber includes providing each respective sensitive content signal of the one or more sensitive content signals to a different transcriber of a plurality of transcribers.

12. The computer program product of claim 10, wherein the operations further comprise:
providing the one or more non-sensitive content signals to the second transcriber.

13. A computing system comprising:
a memory; and
a processor configured to receive an input speech signal by utilizing one or more of a plurality of discrete audio acquisition devices to form an audio recording beam, thus enabling capturing of the input speech signal produced by an encounter participant as at least one audio acquisition device is directed toward the encounter participant, wherein the processor is further configured to generate, via an automated speech recognition (ASR) system, a transcription of the input speech signal, wherein the processor is further configured to identify one or more splitting points between one or more sensitive content portions and one or more non-sensitive content portions from the transcription, wherein the processor is further configured to split the input speech signal into the one or more sensitive content portions and the one or more non-sensitive content portions utilizing a splitting system based upon, at least in part, the one or more splitting points, thus defining one or more sensitive content signals and one or more non-sensitive content signals, wherein the processor is further configured to provide the one or more sensitive content signals to a first set of transcribers of a plurality of transcribers, wherein providing the one or more sensitive content signals to the first set of transcribers includes providing each respective sensitive content signal of the one or more sensitive content signals to a different transcriber of the plurality of transcribers, wherein the processor is further configured to provide the one or more non-sensitive content signals to a second set of transcribers, wherein the processor is further configured to process a transcription of the one or more sensitive content signals generated by a first transcriber, thus defining a sensitive content transcription, wherein the processor is further configured to process a transcription of the one or more non-sensitive content signals generated by a second transcriber, thus defining a non-sensitive content transcription, wherein the processor is further configured to generate a combined transcription by combining the sensitive content transcription and the non-sensitive content transcription and by utilizing a splitting signal from the splitting system to synchronize the sensitive content transcription and the non-sensitive content transcription when generating the combined transcription, wherein the processor is further configured to train a speech processing model based upon, at least in part, the combined transcription and the input speech signal originally containing the one or more sensitive content portions for training data, wherein the combined transcription acts as labeled data for the input speech signal without disclosing all of the input speech signal to either the first transcriber or the second transcriber, and wherein the processor is further configured to process speech input using the trained speech processing model.

14. The computing system of claim 13, wherein the one or more sensitive content portions include one or more of:
  personally identifiable information (PII); and
  protected health information (PHI).

15. The computing system of claim 13, wherein the processor is further configured to: modify one or more properties of the input speech signal to disguise personal identification information within the input speech signal.

\* \* \* \* \*